(12) United States Patent
Wixey et al.

(10) Patent No.: US 7,552,854 B2
(45) Date of Patent: Jun. 30, 2009

(54) SURGICAL STAPLER WITH FIRING LOCK MECHANISM

(75) Inventors: Matthew A. Wixey, Dana Point, CA (US); Gary M. Johnson, Mission Viejo, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 11/805,094

(22) Filed: May 21, 2007

(65) Prior Publication Data

US 2007/0278277 A1    Dec. 6, 2007

Related U.S. Application Data

(60) Provisional application No. 60/747,790, filed on May 19, 2006.

(51) Int. Cl.
*B25C 5/02* (2006.01)

(52) U.S. Cl. .............. 227/175.4; 227/175.2; 227/19

(58) Field of Classification Search .............. 227/175.1, 227/19, 175.4, 175.2, 177.1, 181.1, 182.1
See application file for complete search history.

(56) References Cited

U.S. PATENT DOCUMENTS

| | | | |
|---|---|---|---|
| 2,073,960 A | 3/1937 | Crosby | |
| 2,140,593 A | 12/1938 | Pankonin | |
| 2,351,608 A | 6/1944 | Greenwood | |
| 2,487,565 A | 11/1949 | Leber et al. | |
| 2,641,154 A | 6/1953 | Heller | |
| 3,076,373 A | 2/1963 | Matthews | |
| 3,077,812 A | 2/1963 | Dietrich | |
| 3,080,564 A | 3/1963 | Stekopitov et al. | |
| 3,203,220 A | 8/1965 | Kaepernik | |
| 3,252,643 A | 5/1966 | Stekopitov et al. | |
| 3,273,562 A | 9/1966 | Brown | |
| 3,373,646 A | 3/1968 | Ehlert | |
| 3,494,533 A | 2/1970 | Green et al. | |
| 3,675,688 A | 7/1972 | Bryan et al. | |
| 3,692,224 A | 9/1972 | Astafiev et al. | |
| 4,261,244 A | 4/1981 | Becht et al. | |
| 4,281,785 A | 8/1981 | Brooks | |
| 4,317,451 A | 3/1982 | Cerwin et al. | |
| 4,407,286 A | 10/1983 | Noiles et al. | |
| 4,434,796 A | 3/1984 | Karapetian et al. | |
| 4,442,964 A | 4/1984 | Becht | |
| 4,454,875 A | 6/1984 | Pratt et al. | |
| 4,522,327 A | 6/1985 | Korthoff et al. | |
| 4,527,724 A | 7/1985 | Chow et al. | |

(Continued)

FOREIGN PATENT DOCUMENTS

EP    0251444    1/1988

(Continued)

*Primary Examiner*—Brian D Nash
(74) *Attorney, Agent, or Firm*—John F. Heal; David G. Majdali; Patrick Y. Ikehara

(57) ABSTRACT

A surgical stapler is provided that maintains the jaws of the stapler in an open position and prevents firing of staples when a cartridge is not loaded in one of the jaws. Distinct positioning and sequencing of the jaws, capture pin and firing of the staples are provided by a latch mechanism. Such locking and latching mechanisms ensure proper operation of the stapler.

12 Claims, 34 Drawing Sheets

U.S. PATENT DOCUMENTS

| | | |
|---|---|---|
| 4,589,582 A | 5/1986 | Bilotti |
| 4,591,085 A | 5/1986 | Di Giovanni |
| 4,728,020 A | 3/1988 | Green et al. |
| 4,892,244 A | 1/1990 | Fox et al. |
| 4,923,350 A | 5/1990 | Hinksman et al. |
| 4,955,959 A | 9/1990 | Tompkins et al. |
| 5,031,814 A | 7/1991 | Tompkins et al. |
| 5,065,929 A | 11/1991 | Schulze et al. |
| 5,071,052 A | 12/1991 | Rodak et al. |
| 5,106,008 A | 4/1992 | Tompkins et al. |
| 5,116,349 A | 5/1992 | Aranyi |
| 5,129,570 A | 7/1992 | Schulze et al. |
| 5,201,746 A | 4/1993 | Shichman |
| 5,221,036 A | 6/1993 | Takase |
| 5,236,440 A | 8/1993 | Hlavacek |
| 5,240,163 A | 8/1993 | Stein et al. |
| RE34,519 E | 1/1994 | Fox et al. |
| 5,275,323 A | 1/1994 | Schulze et al. |
| 5,289,963 A | 3/1994 | McGarry et al. |
| 5,307,976 A | 5/1994 | Olson et al. |
| 5,350,400 A | 9/1994 | Esposito et al. |
| 5,364,002 A | 11/1994 | Green et al. |
| 5,366,479 A | 11/1994 | McGarry et al. |
| 5,397,046 A | 3/1995 | Savage et al. |
| 5,413,267 A | 5/1995 | Solyntjes et al. |
| 5,439,155 A | 8/1995 | Viola |
| 5,439,479 A | 8/1995 | Shichman et al. |
| 5,445,304 A | 8/1995 | Plyley et al. |
| 5,458,279 A | 10/1995 | Plyley |
| 5,462,215 A | 10/1995 | Viola et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,472,132 A | 12/1995 | Savage et al. |
| 5,480,089 A | 1/1996 | Blewett |
| 5,497,933 A | 3/1996 | DeFonzo et al. |
| 5,509,596 A | 4/1996 | Green et al. |
| 5,509,920 A | 4/1996 | Phillips et al. |
| 5,547,117 A | 8/1996 | Hamblin et al. |
| 5,558,266 A | 9/1996 | Green et al. |
| 5,579,978 A | 12/1996 | Green et al. |
| 5,580,067 A | 12/1996 | Hamblin et al. |
| 5,584,425 A | 12/1996 | Savage et al. |
| 5,605,272 A | 2/1997 | Witt et al. |
| 5,630,539 A | 5/1997 | Plyley et al. |
| 5,636,779 A | 6/1997 | Palmer |
| 5,673,842 A | 10/1997 | Bittner et al. |
| 5,678,748 A | 10/1997 | Plyley |
| 5,680,983 A | 10/1997 | Plyley et al. |
| 5,706,998 A | 1/1998 | Plyley et al. |
| 5,709,334 A | 1/1998 | Sorrentino et al. |
| 5,715,988 A | 2/1998 | Palmer |
| 5,718,359 A | 2/1998 | Palmer et al. |
| 5,735,445 A | 4/1998 | Vidal et al. |
| 5,762,255 A | 6/1998 | Chrisman et al. |
| 5,785,232 A | 7/1998 | Vidal et al. |
| 5,794,834 A | 8/1998 | Hamblin et al. |
| 5,810,240 A | 9/1998 | Robertson |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,918,791 A | 7/1999 | Sorrentino et al. |
| 5,988,479 A | 11/1999 | Palmer |
| 6,079,606 A | 6/2000 | Milliman et al. |
| 6,109,500 A | 8/2000 | Alli et al. |
| 6,131,789 A | 10/2000 | Schulze et al. |
| 6,155,473 A | 12/2000 | Tompkins et al. |
| 6,488,196 B1 | 12/2002 | Fenton, Jr. |
| 6,569,171 B2 | 5/2003 | DeGuillebon et al. |
| 2002/0025243 A1 | 2/2002 | Heck |
| 2002/0029044 A1 | 3/2002 | Monassevitch et al. |
| 2002/0120279 A1 | 8/2002 | Deguillebon et al. |
| 2004/0006372 A1 | 1/2004 | Racenet et al. |
| 2004/0138705 A1 | 7/2004 | Heino et al. |

FOREIGN PATENT DOCUMENTS

| | | |
|---|---|---|
| EP | 492283 A1 | 7/1992 |
| EP | 514139 A2 | 11/1992 |
| EP | 536903 A2 | 4/1993 |
| EP | 596543 A1 | 5/1994 |
| WO | WO 83/02247 | 7/1983 |
| WO | WO 02/30296 | 4/2002 |

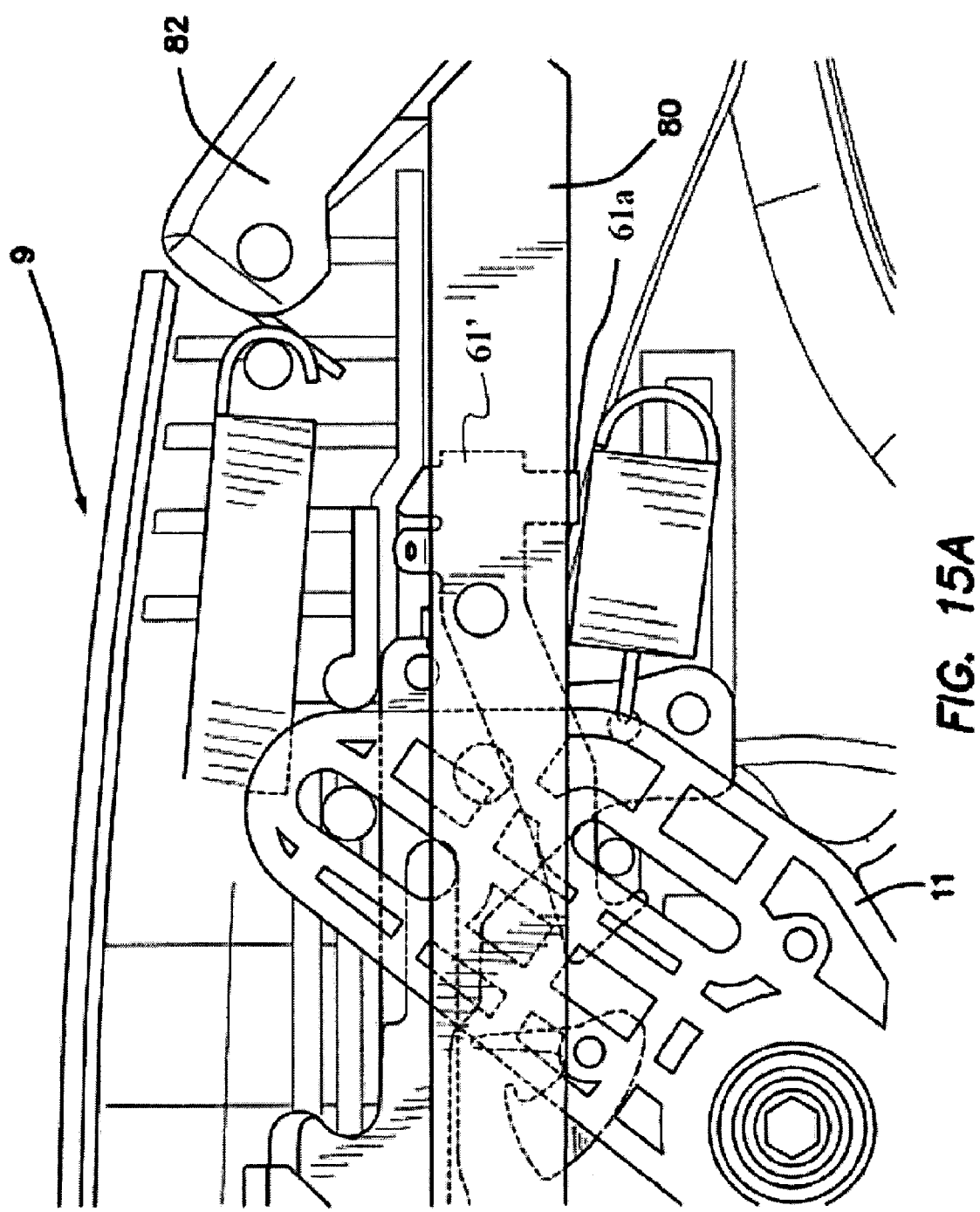

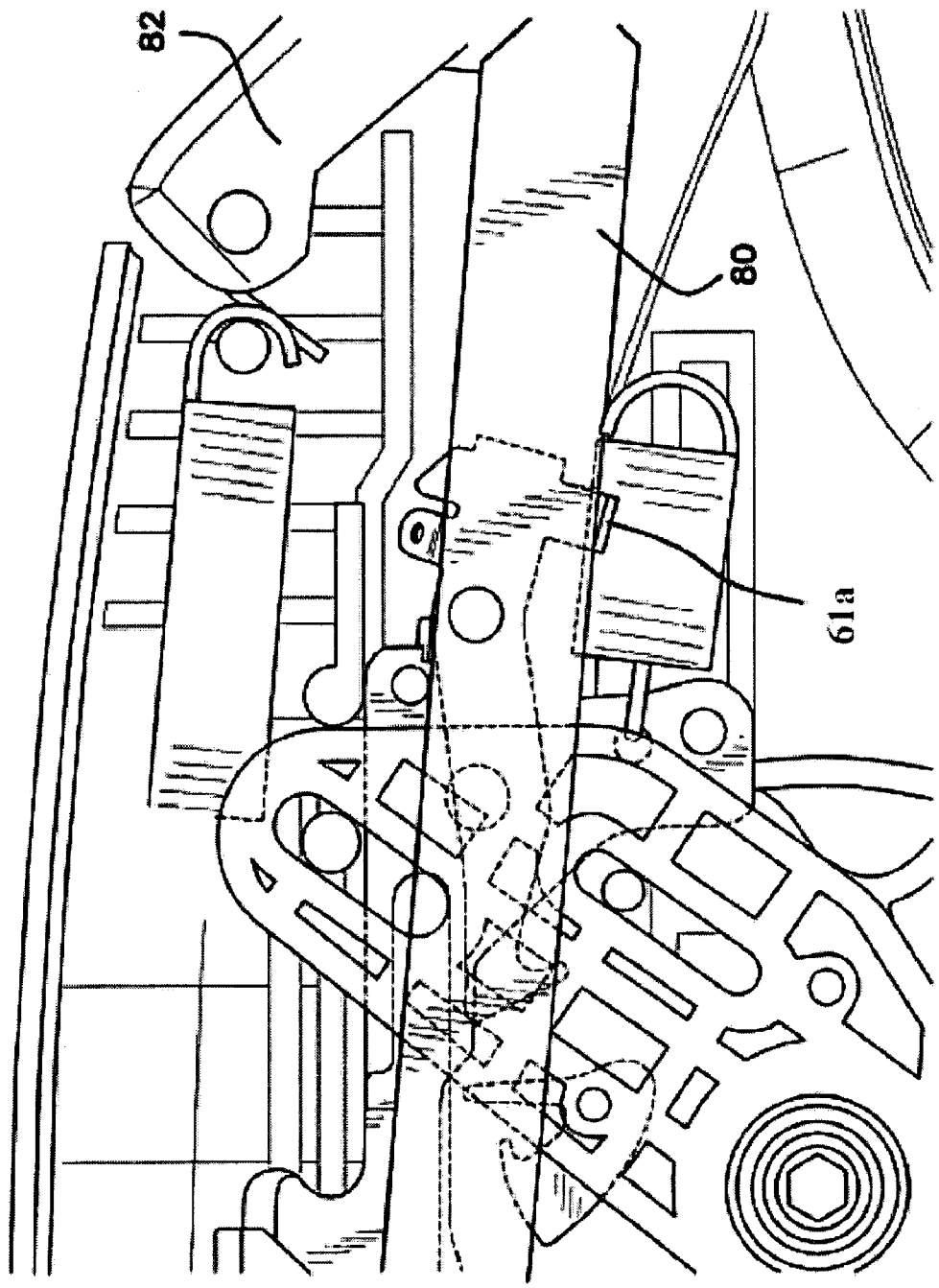

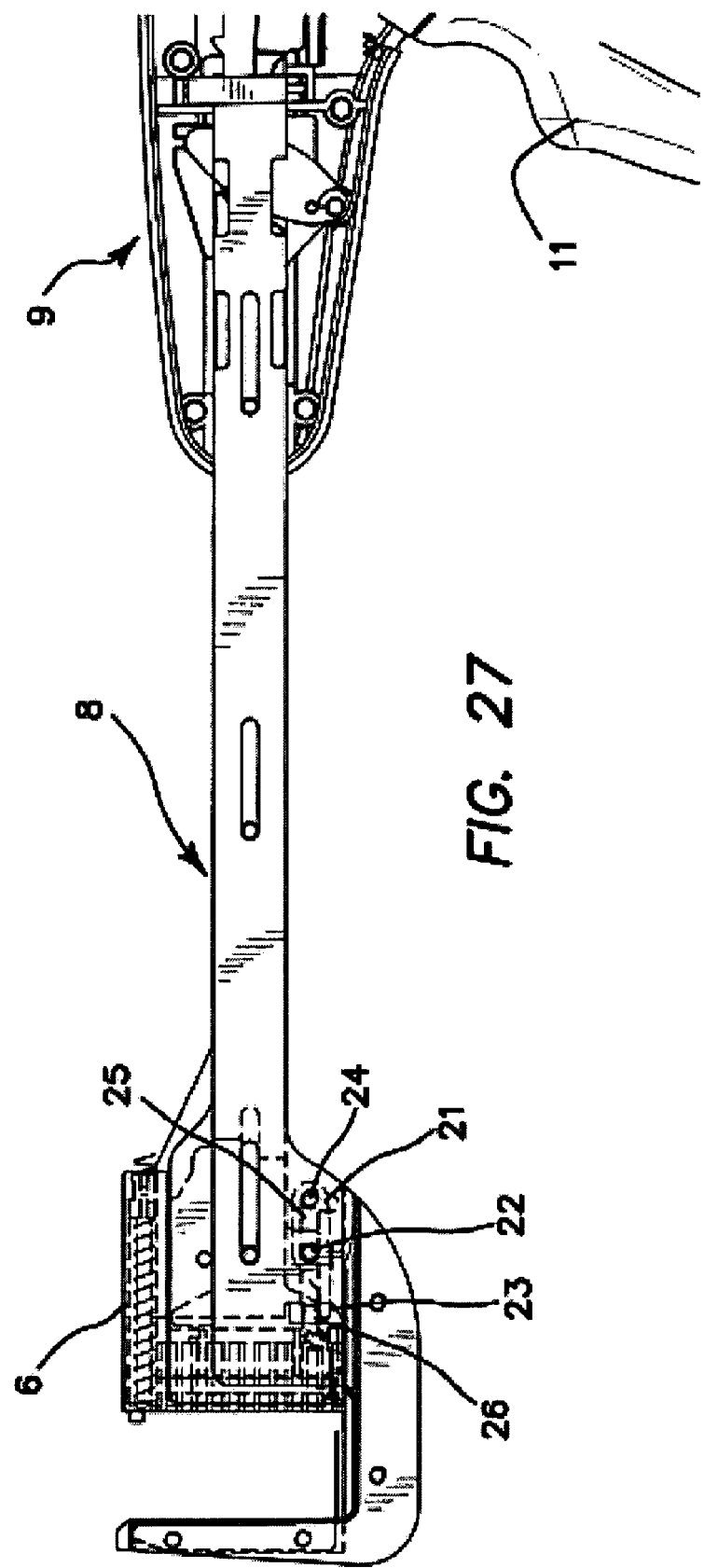

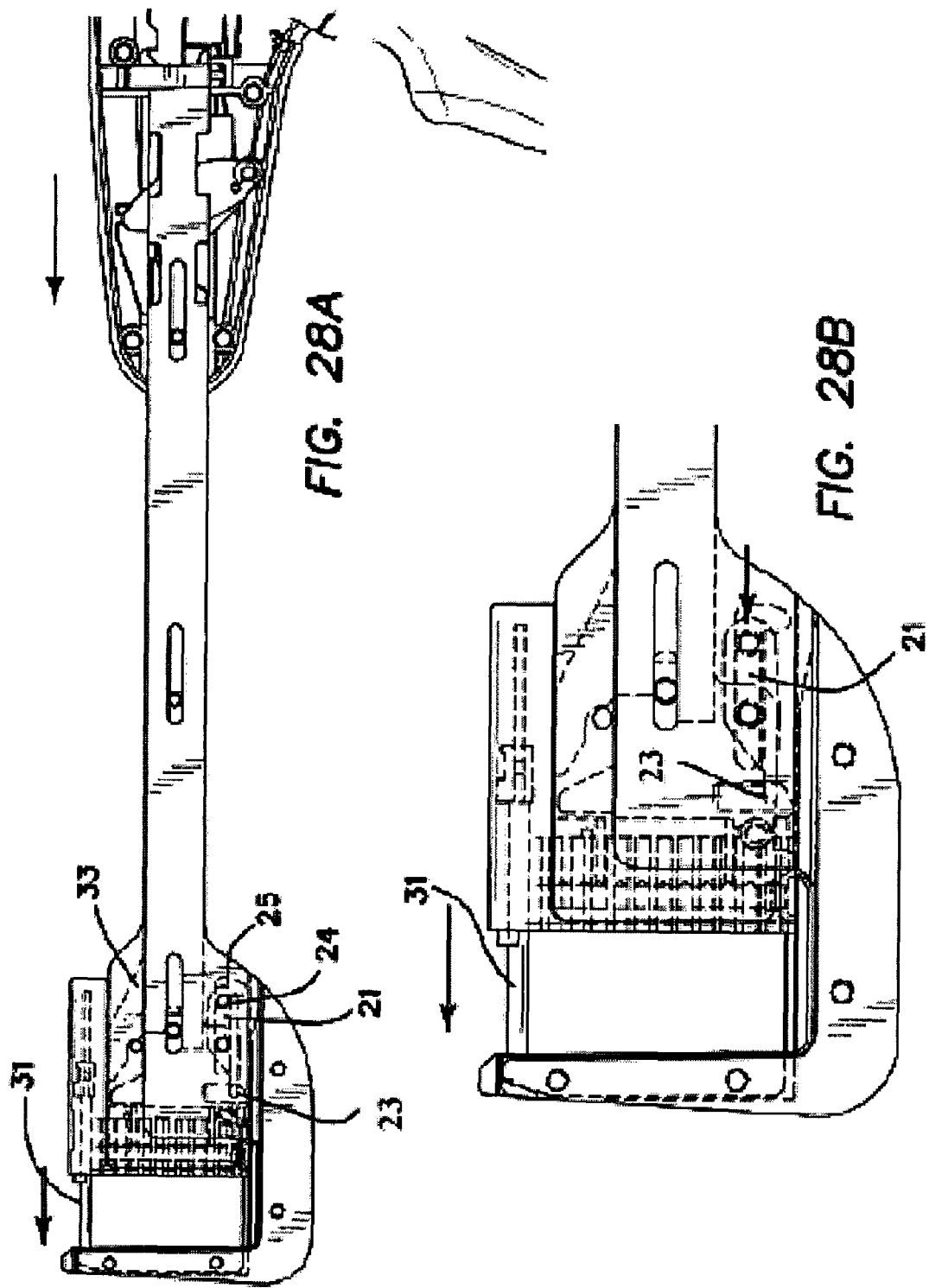

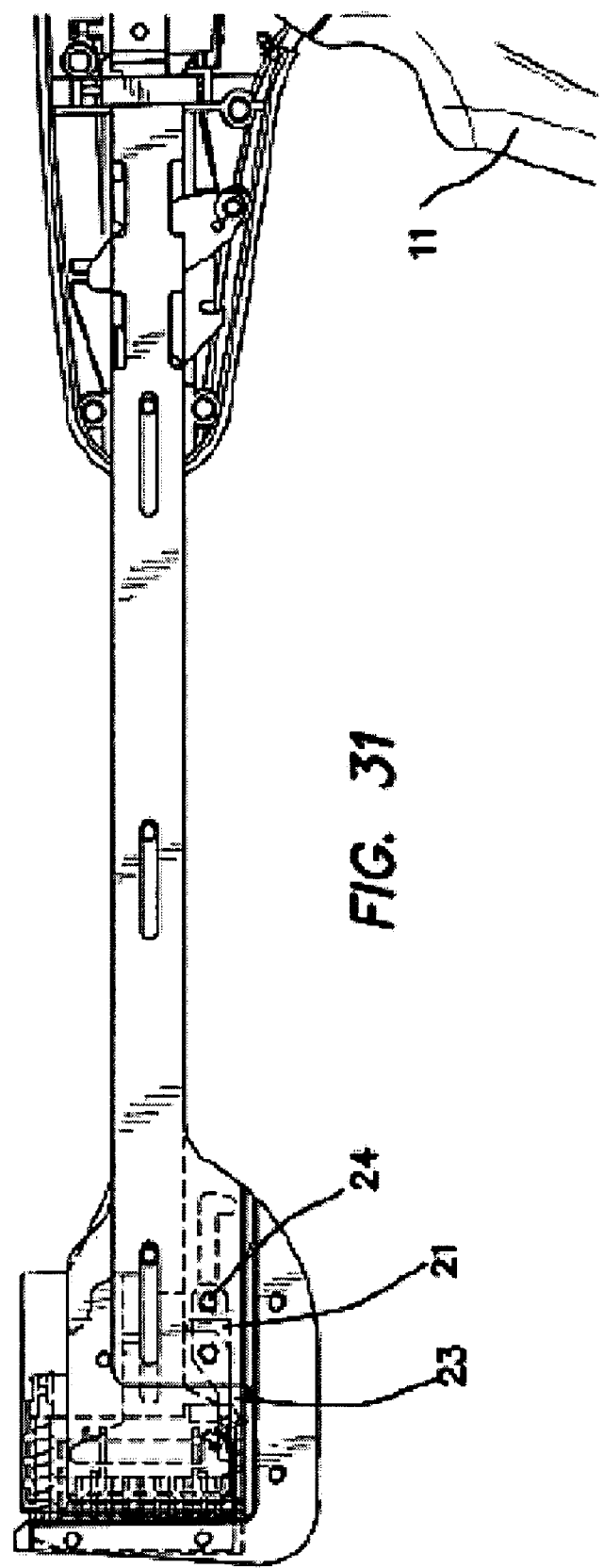

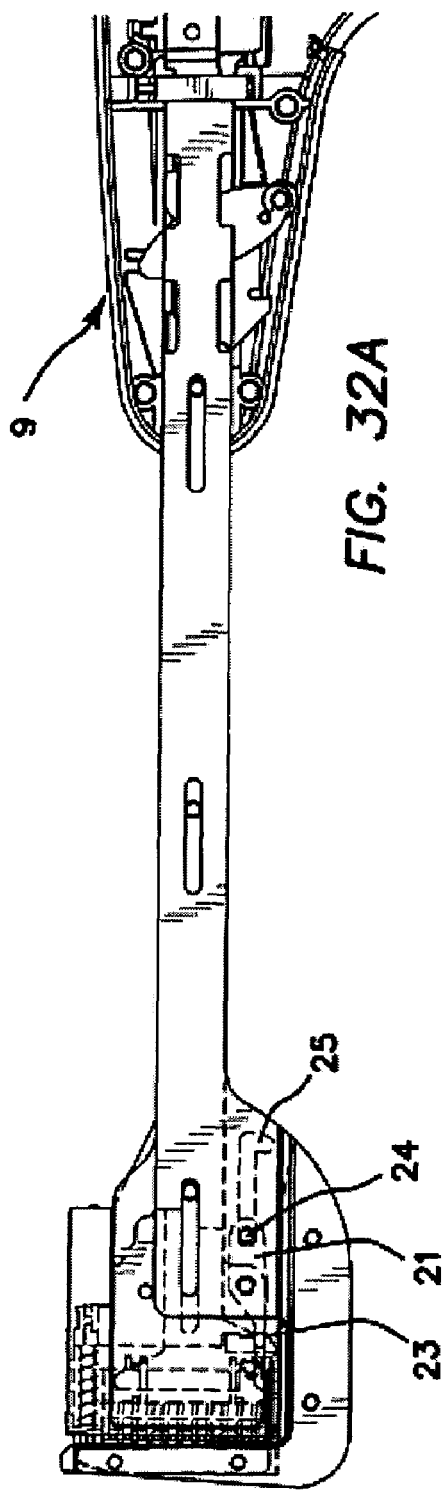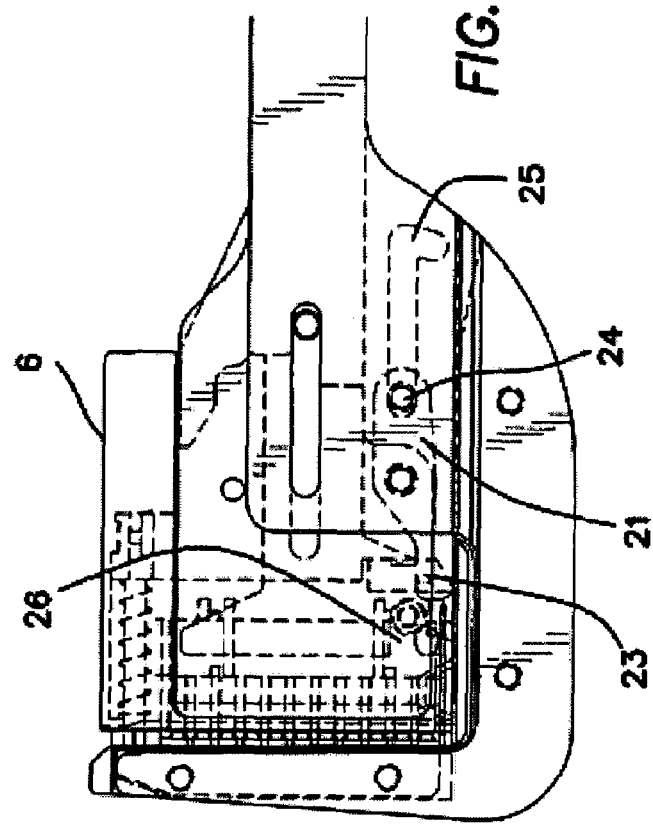

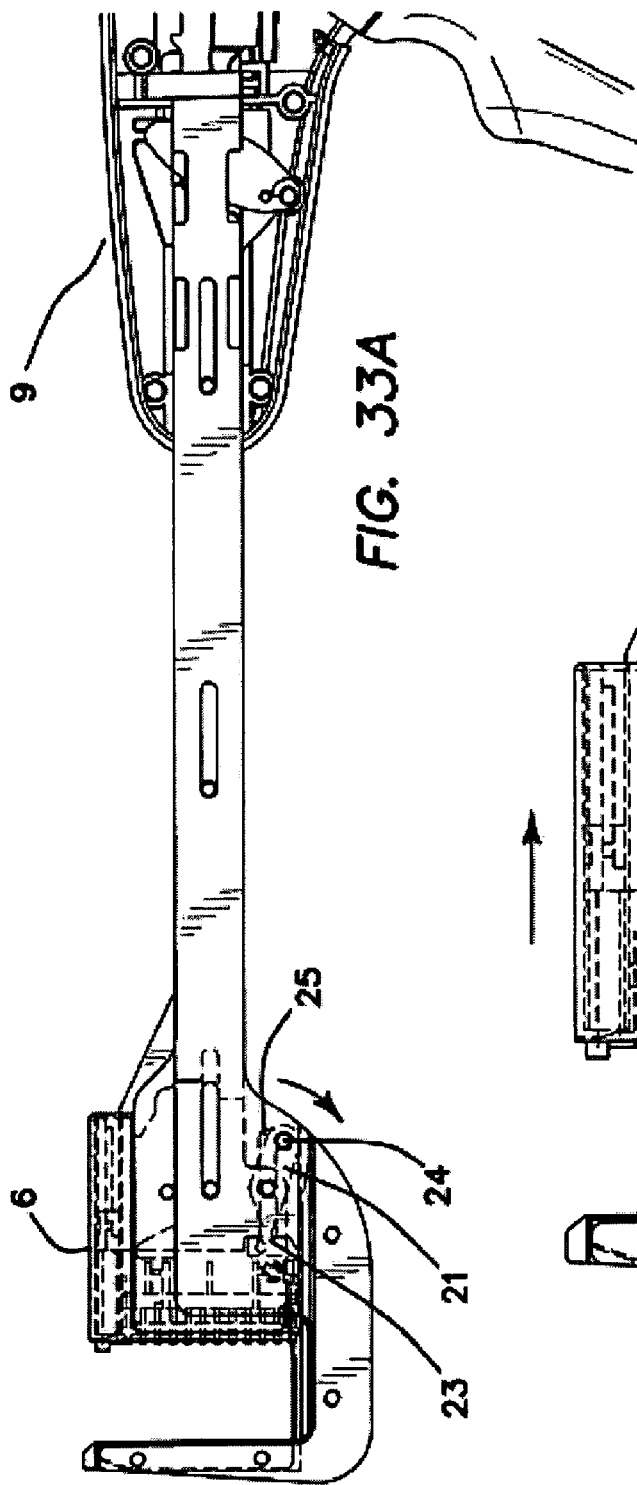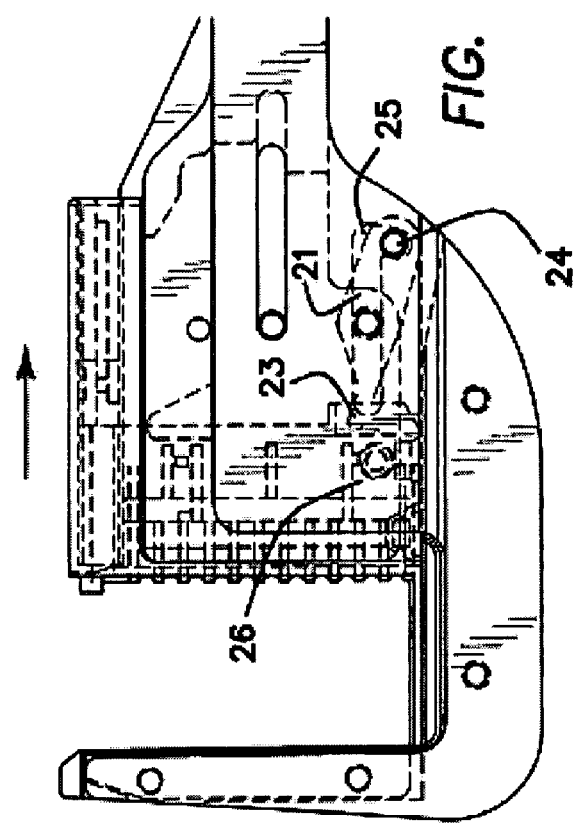

SURGICAL STAPLER WITH FIRING LOCK MECHANISM

CROSS-REFERENCE TO RELATED APPLICATIONS

This application claims the benefit of U.S. Provisional Application No. 60/747,790, filed May 19, 2006, the disclosure of which is hereby incorporated by reference as if set forth in full herein.

BACKGROUND

The present invention relates generally to surgical occlusion instruments and, more particularly, to surgical staplers.

Surgical staplers are used to approximate or clamp tissue and to staple the clamped tissue together. As such, surgical staplers have mechanisms to ensure that tissue is properly positioned and captured prior to driving staples through the tissue. This partly entails that the clamped tissue together is compressed or squeezed to ensure that the width of the clamped tissue is not too large so as to prevent the staples from forming against the anvil of the stapler as well as not too narrow as to eliminate capillary function in the clamped tissue. Mechanisms have also been provided to ensure that staples are loaded in the stapler prior to clamping the tissue.

As a result, this has produced, for example, multiple triggers and handles in conjunction with complex mechanism to provide proper stapling of the clamped tissue. With these complex mechanism, these mechanism increase manufacturing burdens, introduces potential sources for device failure and confusion for the user. Thus, reliable stapling of clamped tissue without complex mechanisms is desired.

SUMMARY

Generally, a surgical stapler is provided. In one aspect, a surgical stapler comprises a shaft, an actuator and a staple pusher. The shaft extends along a longitudinal axis having a proximal end and a distal end, a first jaw and a second jaw extending from the distal end of the shaft. The second jaw is arranged to receive a staple cartridge having a plurality of staples and is movable along the longitudinal axis towards the first jaw. The actuator is coupled to the proximal end of the shaft. The staple pusher is coupled to the actuator and is movable along the longitudinal axis to push the plurality of staples out of the cartridge along the longitudinal axis. The staple pusher has a distal portion pivotally connected to a proximal portion. The distal portion has a first position and a second position with the first position preventing movement of the staple pusher towards the first jaw.

In one aspect, a surgical stapler comprises a shaft, an actuator and a staple pusher. The shaft extends along a longitudinal axis having a proximal end and a distal end, a first jaw and a second jaw extending from the distal end of the shaft. The second jaw is arranged to receive a staple cartridge having a plurality of staples and is movable towards the first jaw along the longitudinal axis. The actuator is coupled to the proximal end of the shaft. The staple pusher is coupled to the actuator and is movable along the longitudinal axis to push the plurality of staples out of the cartridge along the longitudinal axis. The surgical stapler also comprises means for preventing longitudinal movement of the staple pusher.

In one aspect, a stapler comprises a shaft and an actuator. The shaft has a distal end with a first jaw connected to an anvil, a movable second jaw arranged to receive a staple cartridge and a staple pusher movable within the second jaw. The second jaw is movable towards the first jaw in a longitudinal direction. The actuator is connected to a proximal end of the shaft and has a movable trigger connected to a stationary handle housing. A firing lever is encased in the stationary handle housing and the firing lever has a hook operationally connected to a projection extending from the staple pusher.

Many of the attendant features of the present invention will be more readily appreciated as the same becomes better understood by reference to the foregoing and following description and considered in connection with the accompanying drawings in which like reference symbols designate like parts throughout.

BRIEF DESCRIPTION OF THE DRAWINGS

FIGS. 27-35 are side views of a surgical stapler in accordance with various aspects of the present invention.

DETAILED DESCRIPTION

Figure 1:
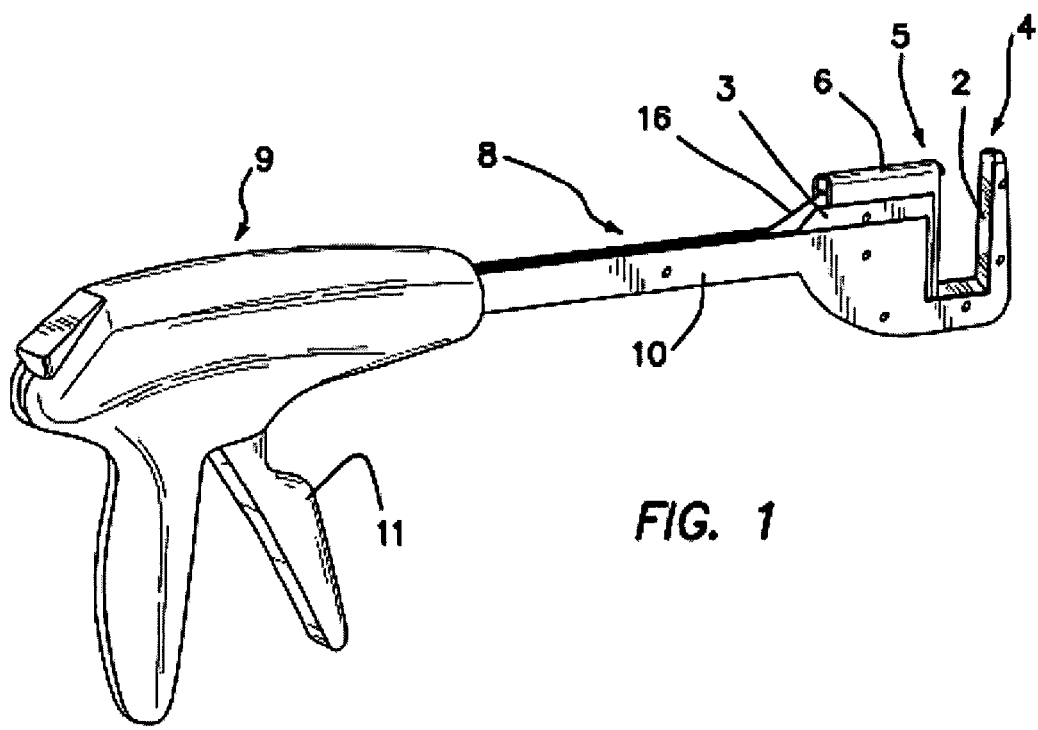
FIG. 1 is a perspective view of a surgical stapler in accordance with various aspects of the present invention.
Figure 2A:
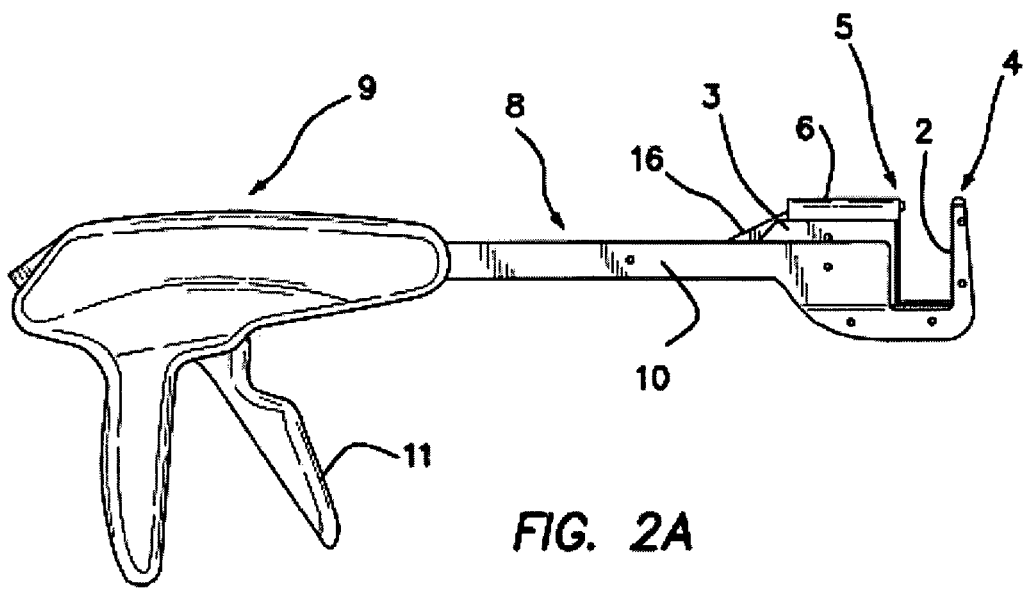
FIG. 2A is a side view of a surgical stapler in accordance with various aspects of the present invention.
Figure 2B:
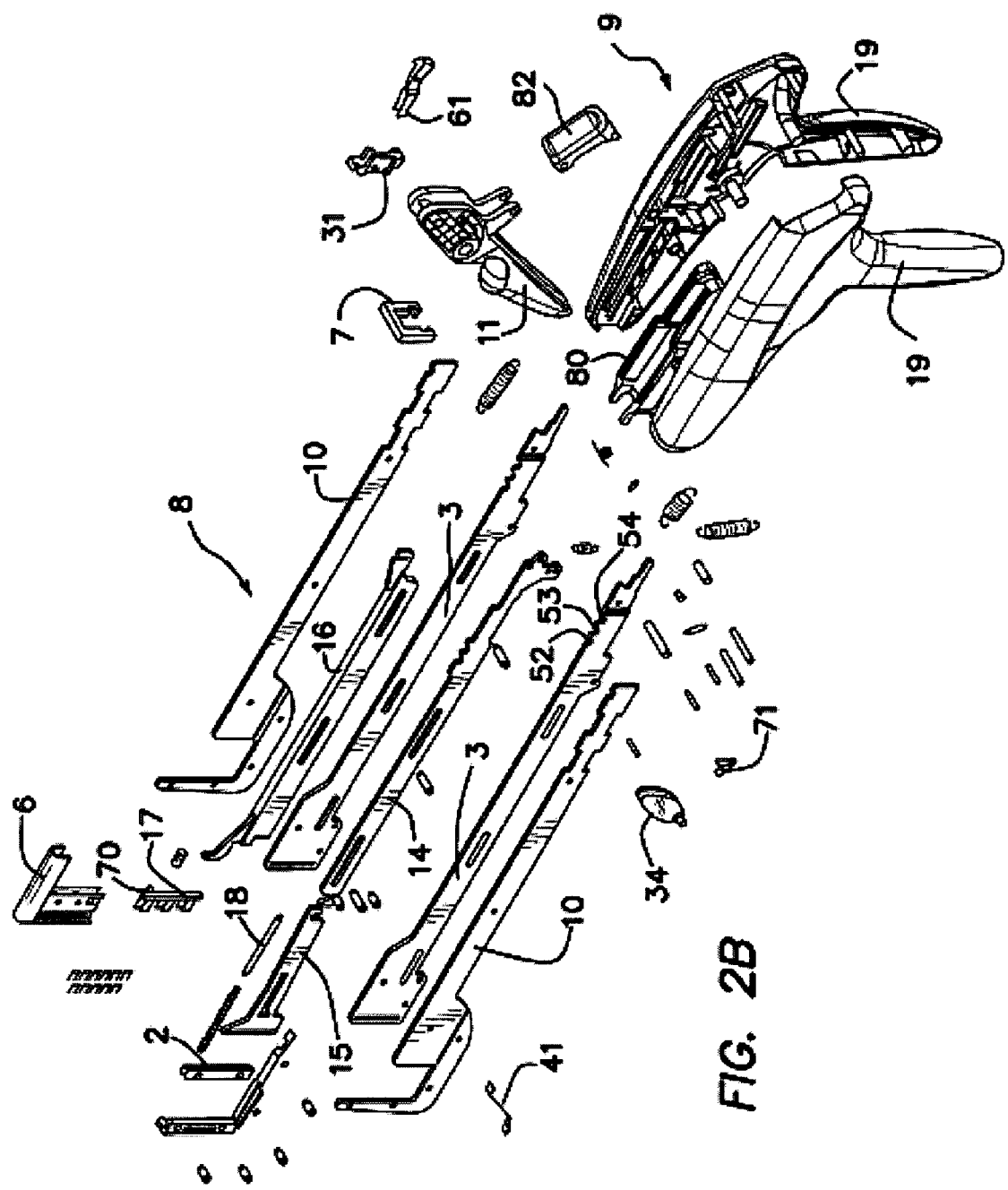
FIG. 2B is a exploded view of a surgical stapler in accordance with various aspects of the present invention.
Figure 2C:
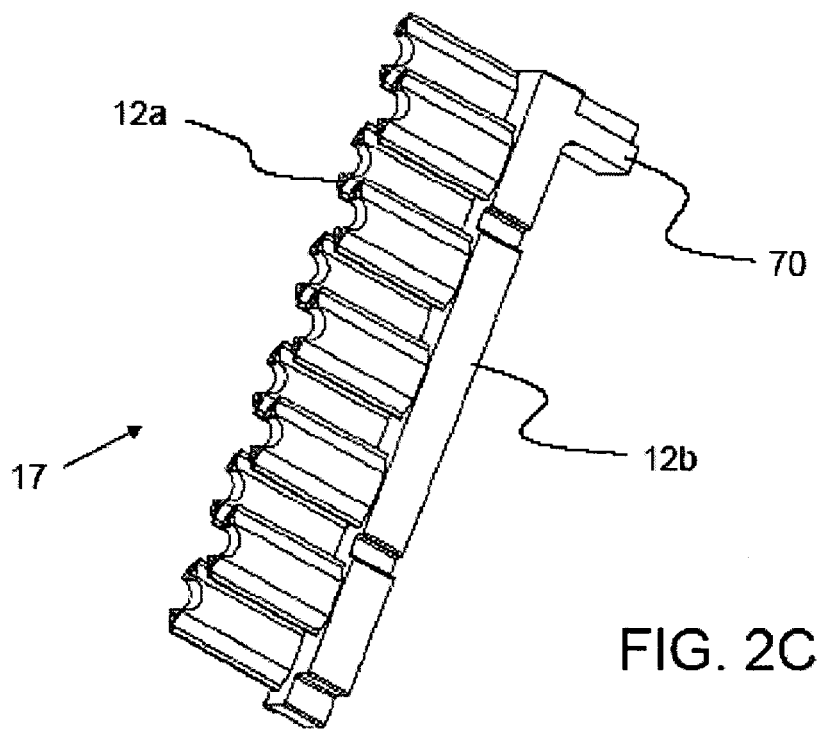
FIG. 2C is an enlarged perspective view of staple drivers in accordance with various aspects of the present invention.
Figure 2D:
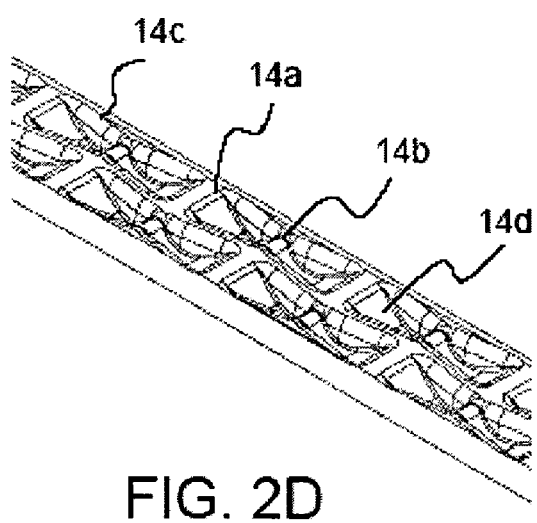
FIG. 2D is an enlarged top view of an anvil in accordance with various aspects of the present invention.
Figure 2E:
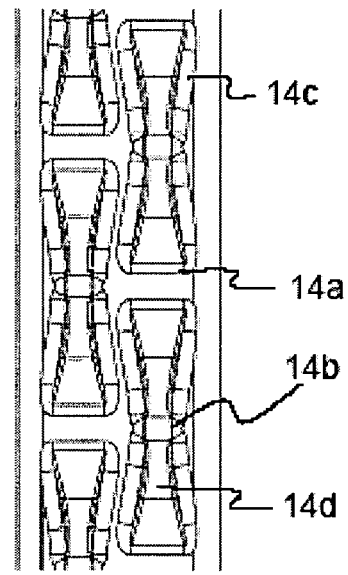
FIG. 2E is an enlarged perspective view of an anvil in accordance with various aspects of the present invention.

In FIGS. 1-2, a surgical stapler has a barrel or shaft 8 extending along a longitudinal axis with an actuator 9 connected to a proximal end of the shaft. End effectors or jaws 4,5 are integrally formed or extend from a distal end of the shaft 8. Disposed on jaws 4,5 are an anvil 2 and a cartridge 6. In one aspect, the anvil 2 is disposed on jaw 4, which is stationary and is integrated with frame 10 of the shaft 8. The cartridge support 3, part of jaw 5, is movable and is arranged to receive the removable cartridge 6. The cartridge contains one or more staples or fasteners and one or more staple drivers 17 such that when pressure is applied to the staple drivers 17, the staples are ejected or fired from the cartridge 6 through tissue clamped or compressed between the jaws 4,5. A staple pusher 14,15 provides or communicates the pressure to fire the staples. In one aspect, the staple drivers 12 has at least one distal surface 12a arranged to drive a staple out of the staple cartridge and at least one proximal surface 12b arranged to contact the distal portion of the staple pusher 14,15. The distal portion of the staple pusher in one aspect has an enlarged end arranged to contact the at least one proximal surface of the staple driver.

The shaft 8 comprises the staple pusher 14,15, the cartridge holder, retainer or support 3, frame 10 and a capture pin pusher 16. The frame 10 is fixed to the actuator 9. The staple pusher 14,15, the cartridge support 3 and capture pin pusher 16 are movable relative to the frame 10 and the actuator 9 traversing along a longitudinal axis of the surgical stapler. In one aspect, the cartridge support comprises two symmetrical elongate shafts or slides connected together on a proximal end by a support block case 31. The block case 31 in one aspect provides a hook or post from which a spring 91 is attached on one end and connected to the actuator 9 on the other end. The spring biases the cartridge support 3 via the block case proximally or away from the anvil 2 and towards the actuator 9. The distal end of cartridge support 3 defines an opening arranged to receive the cartridge 6 and in one aspect extends or spreads orthogonally from the two side plates, slides or elongate shafts forming an enlarged "T" or "hammer head" like shape or profile.

The frame 10 defines a channel through which the cartridge support 3 moves, e.g., slides longitudinally relative to the actuator 9. The cartridge support 3 with the cartridge 6 moves longitudinally relative to the actuator 9 to capture and clamp tissue between the cartridge and the anvil 2. The cartridge support 3 in one aspect also defines a channel through which the staple pusher 14,15 and the capture pin pusher 16 are disposed and movable therethrough. The staple pusher 14,15 interacts with the cartridge 6 to eject staples from the cartridge 6 by contacting staple drivers 17 within the cartridge 6. In one aspect, the staple pusher 14,15 are attached to a spring 94 which is connected the actuator 9. The spring biases the staple pusher 14,15 proximally or away from the anvil 2 and towards the actuator 9. The capture pin pusher 16 also interacts with the cartridge 6 to cause a spring loaded capture pin 18 situated in the cartridge 6 to extend into or allow retraction from the anvil 2.

The actuator 9 comprises a trigger 11 pivotably coupled to a stationary handle housing 19. The frame 10 in one aspect comprises an elongate body or shaft with one end, a proximal end, fixedly coupled to the actuator 9. The other end of the elongate body of the frame 10 is generally U-shaped with the anvil 2 attached to or extending along the frame on an axis perpendicular to the longitudinal axis of the elongate body of the frame 10. In one aspect, the anvil is integral with the frame 10 forming a monolithic structure. The frame 10 in one aspect comprises symmetrical support blades both fixedly attached together on either end with one end coupled to the actuator 9 and the other end coupled to or forming the anvil 2. Sufficient springs, pins, posts, spacers, slots, detents and other similar components or formations are also provided to secure various components of the stapler together and to facilitate operation of the stapler.

In one aspect, the anvil 2 comprises a plurality of staple pockets having a generally hourglass shape with squared off ends 14a. The width of the middle or center portion 14b is smaller than the width of the ends 14a to facilitate formation of staples driven against the staple pocket. The squared off ends providing a large first contact area directing the staple ends towards the narrow middle portion to form a staple. Two cavities are separated by the middle portion with a slope curving up to the middle portion from each of the staple ends 14a. A sloping surface 14c slopes from the top surface of the anvil 2 and surrounds a trough 14d or pocket for receiving the legs of a staple. The staple is formed as the legs are deflected towards the center portion 14b of the trough. The trough is shallow and slopes downward from the sloping surface 14c but is somewhat raised at its center. The staple in one aspect is symmetrical, e.g., round or square. In one aspect, the staples are flatten along one surface, e.g., the top and/or, along a symmetrically opposing surface, e.g., the bottom. The cross-sectional shape of the staple or periphery is not fully symmetrical, e.g., an oval versus a circle.

In one aspect, the cartridge 6 has a groove or elongate cavity that mates and aligns with a corresponding projection or elongate raised portion in the cartridge support 3 on the stapler. The projection and cavity combination identifies specific cartridge types, e.g., vascular versus non-vascular. The staple drivers or ejectors in the cartridge are provided in three columns extending from a single contact base to simultaneously eject all the staples in the cartridge to form against a corresponding three columns of staple pockets in the anvil.

In operation, a cartridge is loaded in the cartridge support 3 of the stapler. The stapler jaws 4,5 are positioned to place tissue between the jaws 4,5. If the loaded cartridge does not have staples, the trigger 11 is not allowed to move or be actuated. Actuating the trigger 11, after a staple filled cartridge is loaded, causes the capture pin 18 to deploy and the jaws 4,5 to move together. Thus, tissue becomes encased or encompassed between the jaws 4,5/frame 10 and the capture pin 18. As such, the tissue can be initially captured without placing significant pressure or force on the tissue from the jaws 4,5. Users, such as a surgeon, are thereby afforded the options of further fine tuning the positioning of the stapler, leaving the stapler in place to perform other surgical tasks, continue to operate the stapler or start over. Actuating the trigger 11 further causes the cartridge support 3 to move further towards the anvil 2 to partially close the jaws 4,5 and/or clamp tissue. Completing the actuation stroke of the trigger 11 causes the jaws 4,5 to clamp or compress the tissue therebetween.

Unless the actuation stroke of the trigger 11 is completed, the surgical stapler does not permit the firing of staples from the cartridge. From capturing the tissue, partially closing and fully clamping the tissue, the user is provided multiple predetermined set points and positions to appropriately align and position the stapler jaws 4,5 relative to the tissue as desired. A release button 82 is provided, in one aspect, that when actuated allows the stapler to be reset back to the initial or default position, i.e., jaws opened, as desired, to remove or re-position the location of the stapler. The second or subsequent full or complete actuation stroke of the trigger 11 causes the staple pusher 14,15 and staple driver 17 to move and eject the staples from the cartridge 6.

Referring also now to FIGS. 3-12, the predetermined or set positions of the cartridge support 3 relative to the anvil 2 are maintained by latch 7. In one aspect, flat surfaces or edges of the latch 7 interact with slots or notches (e.g., first, second and third slots 52, 53, 54) in the cartridge support 3 to ensure that the cartridge support 3 moves or operates in discrete predetermined positions. The latch in one aspect is generally u-shaped having flat surfaces with a generally square or rectangle cross-section. The positions in one aspect comprise open, capture, closed positions. The sequential movement of the latch in each of the slots 52, 53, 54 ensures the proper positioning of the cartridge relative to the tissue and the anvil to optimally allow the stapler to operate at each position removing the random positioning of the cartridge relative to the anvil. For example, the closed position as predetermined by the latch and slot interaction ensures the distance between the cartridge and the anvil is sufficient to effectively form and secure a staple through a tissue clamped there between. A firing lever 61 operatively engages the staple pusher 14,15 to permit firing of the staples after the jaws are fully closed. In one aspect, the firing lever is an elongate hook or partially curved or slanted elongate lever or anchor. After firing or ejecting the staples from the cartridge, a handle fire lock lever 71 operatively engages the cartridge support 3 to prevent the trigger 11 from opening or moving proximally even if the trigger is released. In one aspect, the fire lock lever 71 is a hook or partially curved or slanted lever or anchor.

Figure 3A:
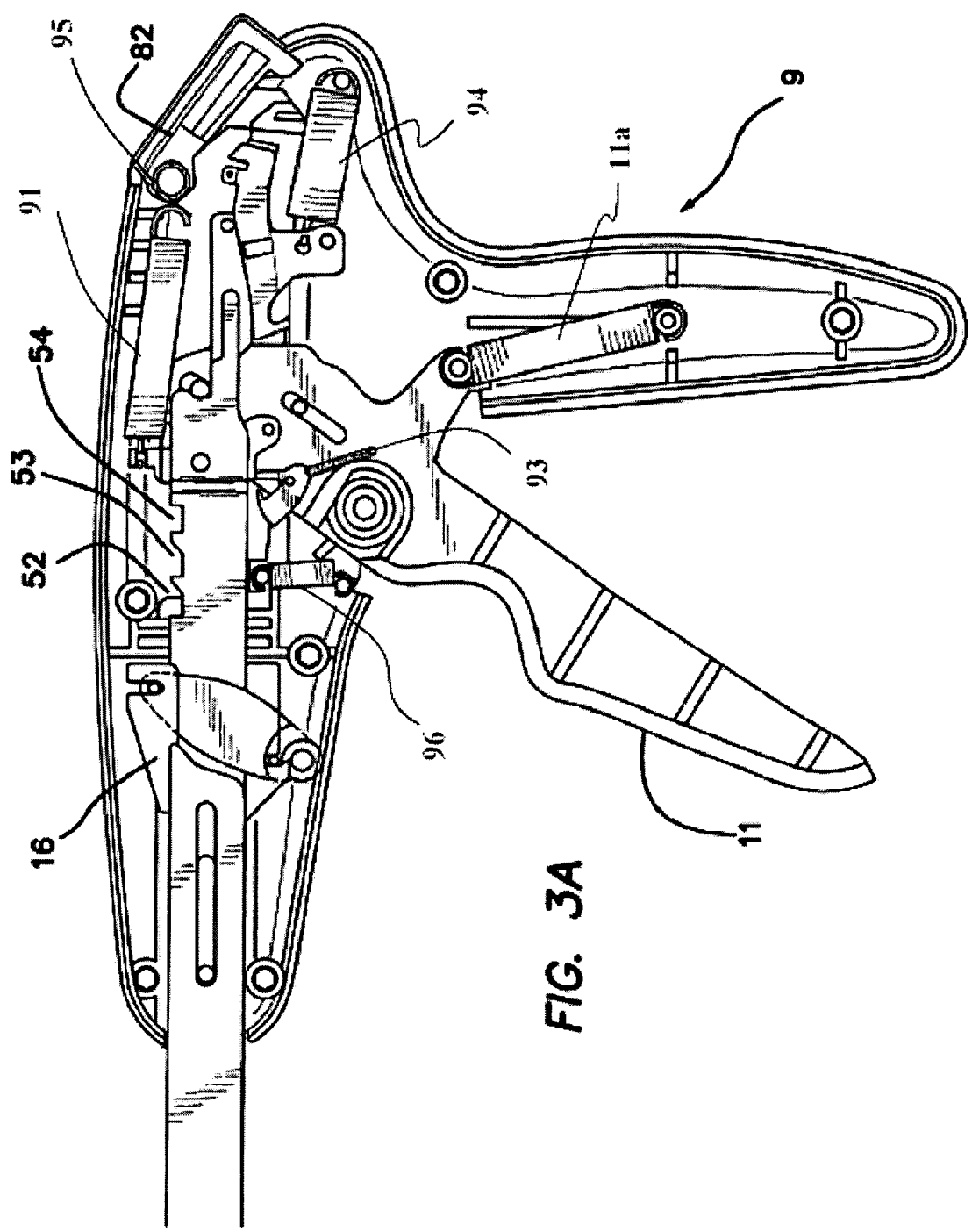
FIGS. 3-12 are side views of a surgical stapler in accordance with various aspects of the present invention.
Figure 3B:
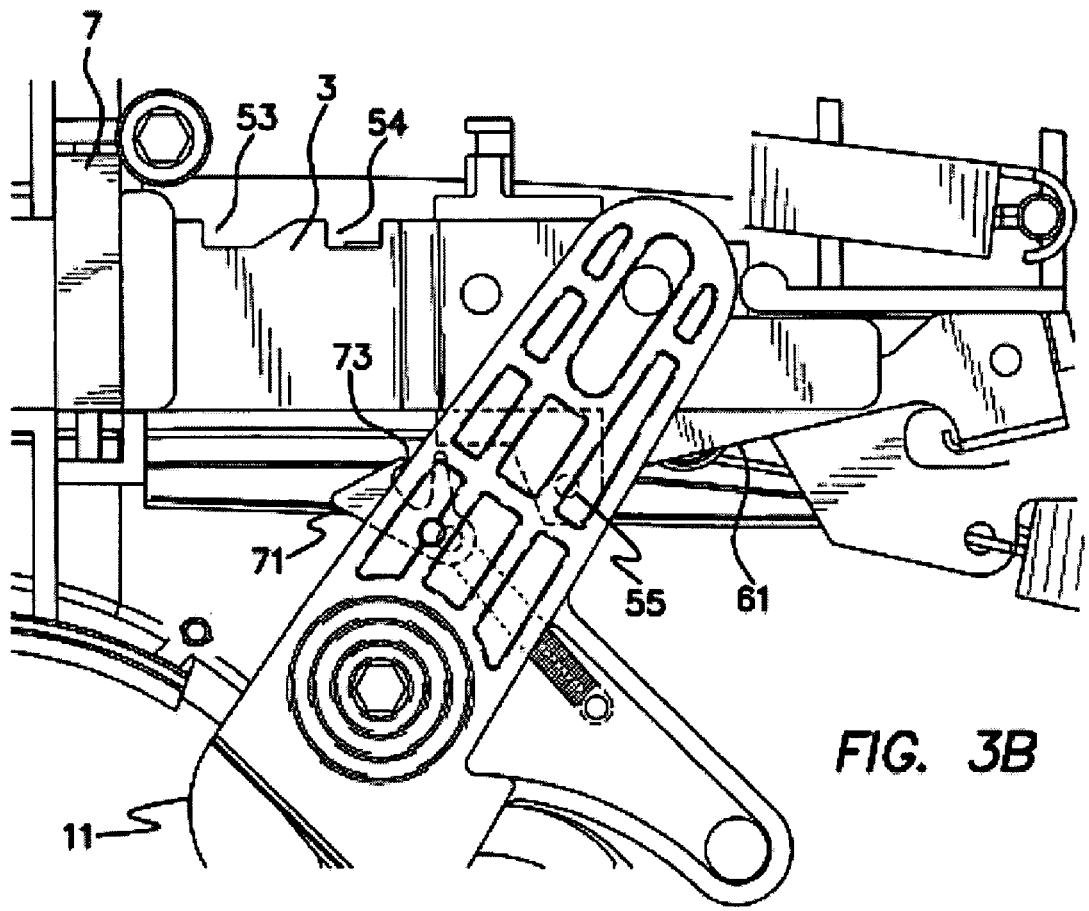

In FIG. 3, the default or open position is shown with latch 7 positioned or riding along a top surface or edge of the cartridge support 3. The trigger 11 of actuator 9 is connected to a post, projection or pin 51 that rests in a cavity or notch of the cartridge support 3, when the stapler is in an open, default, initial or resting position, i.e., the jaws are open to receive tissue there between. In the open position, the latch 7 is not engaged or situated in one of slots 52, 53, 54 on the cartridge support 3. The latch 7 rests or is secured within a cavity or channel disposed in the actuator 9, which restricts longitudinal or horizontal movement of the latch, but allows vertical or perpendicular movement of the latch.

The firing lever 61 is pivotally connected to the actuator 9 on one end and operatively connected to the staple pusher 14,15 on the other end. The other end or tip of the lever 61 moves somewhat freely and is deflected downward or traverse to the longitudinal direction, i.e., prevented from being in a horizontal or longitudinal position, when the jaws 4,5 are in the open position. The firing lever 61 is also coupled to the actuator 9 in one aspect by a spring 92 that biases the lever to the longitudinal position and in a clockwise direction. The handle fire lock lever 71 is also disposed within the actuator and is pivotally connected to the trigger 11 on one end. In one aspect, the fire lock lever 71 is also coupled to the actuator by a spring 93 that biases the lever to a longitudinal or horizontal position and in a clockwise direction. The fire lock lever 71 has a notch 73 arranged to receive a projection, post or pin 55 connected to the cartridge support 3.

In placing the stapler in a capture configuration or position from the open or initial position, the trigger 11 is pulled or actuated. The cartridge support 3 (jaw 5) moves closer to the anvil 2 (jaw 4) via pin 51 coupled to the trigger 11. The latch 7 is longitudinally fixed to the actuator 9 and thereby slides along the surface of the cartridge support 3 as the cartridge support moves towards the anvil 2. After a predetermined distance is traversed, the latch 7 falls into or is biased into a slot 52 in the cartridge support 3. The engagement or interaction of the latch 7 with the cartridge support 3 causes the jaws and thus the cartridge and anvil to maintain the captured position. The capture pin pusher 16 and the corresponding capture pin 18 also move such that the capture pin is deployed from the cartridge 6 into a cavity or opening in the anvil 2. Further description of the capture pin and pusher is described later below.

Figure 4:
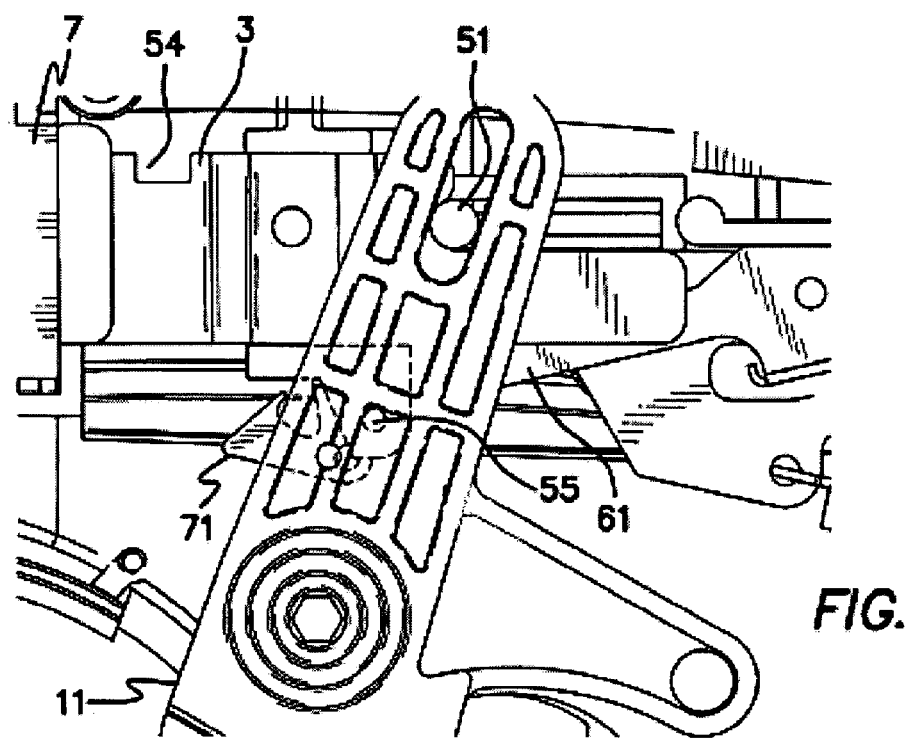

As the trigger 11 is further actuated, the latch 7 rides along the proximal sloped surface of slot 52 to be positioned into the slot 53. With the latch 7 in slot 53 of the cartridge support 3, the partially closed position of the stapler is maintained, without further interaction by the user, e.g., pressure or force is removed from the trigger 11. In FIG. 4, the trigger 11 is pulled or actuated from the capture position. The cartridge support 3 moves distally towards the anvil 2 via pin 51 coupled to the trigger 11 to close or move the jaws 4,5 together, e.g., the jaw 5 with the loaded cartridge is moved closer to the jaw 4 as the cartridge support 3 moves distally. The cartridge support 3 is biased towards the proximal direction away from the anvil 2 and thus resists the distal movement. The latch 7 rides along a surface of the cartridge support 3 as the cartridge support 3 slides by the latch 7. The latch 7 moves into the slot 53 of the cartridge support 3 such that the cartridge support 3 moves sufficiently distally to partially close the jaws 4,5. In other words, a predetermined distance between a starting point of the latch 7 to the slot 53 along the cartridge support 3 corresponds to a predetermined distance between the jaws 4,5 from the capture position to the partially closed position. The engagement or abutment of the latch 7 with the distal edge of slot 53 in the cartridge support 3 along with the interaction of the spring 91 biasing the cartridge support in the proximal direction traps or fixes the cartridge support in position to allow the jaws 4,5 and thus the cartridge and anvil to maintain a partially closed position. The firing lever 61 remains deflected. In the partially closed position, the cartridge support 3 is moved distally and thus the pin 55 is also moved distally but does not yet contact or is received by the fire lock lever 71.

The staple pusher 14,15 is coupled to the cartridge support 3 and as such moves as the cartridge support 3 moves. Also, in one aspect, the pin 51 coupled to trigger 11 is operatively coupled to the staple pusher 14,15. The staple pusher 14,15 is further coupled to the latch 7 and in one aspect biased by a spring 91 coupled to the actuator 9 on one end and connected to the proximal end 62 of the staple pusher. The spring 91 biases the staple pusher in a proximal direction or away from the anvil 2. In one aspect, the staple pusher 14,15 has the same or less number of slots than the cartridge support 3. The slots in the staple pusher 14,15 are similar in size and shape to the slots in the cartridge support 3. Thus, as the trigger 11 is actuated, the staple pusher 14,15 moves and follows the movement of the cartridge support 3. Likewise, as the latch 7 maintains the position of the cartridge support 3, the position of the staple pusher 14,15 is also maintained via slots in the staple pusher or in one aspect the connection to the cartridge support 3.

Figure 5:
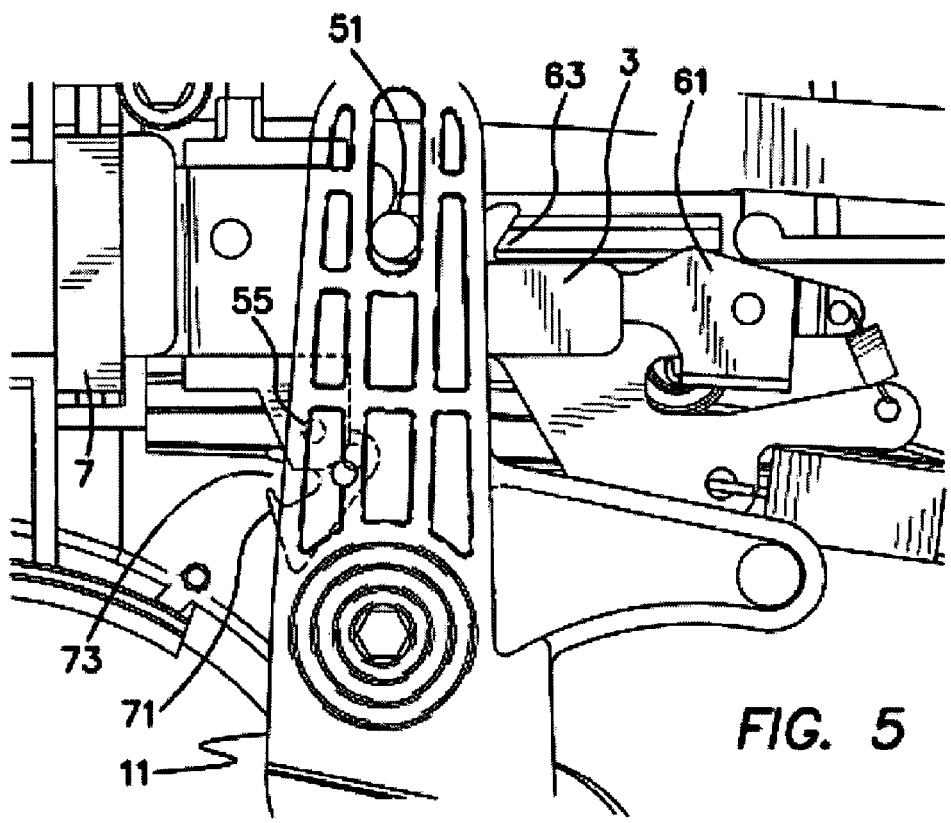

In FIG. 5, the trigger 11 is fully actuated or pulled, e.g., a full or complete actuation stroke, and as such the cartridge support 3 is moved distally via pin 51 to close or move the jaws 4,5 together. The latch 7 rides along the proximal sloped surface of the slot 53 and then moves into the slot 54 as the cartridge support 3 moves sufficiently distal or along a predetermined distance to fully close the jaws 4,5. The engagement or abutment of the edge or surfaces of latch 7 with the distal edge of slot 54 in the cartridge support 3 along with the interaction of the spring 91 biasing the cartridge support 3 in the proximal direction maintains the cartridge support in position thereby maintaining the jaws 4,5, the cartridge and anvil, in a closed or clamped position.

The firing lever 61 becomes unobstructed and thus moves to a horizontal position or aligns longitudinally with the cartridge support 3. In one aspect, pin 51 moves and thus the firing lever is unobstructed. Biased by spring 92, the firing lever pivots into longitudinal alignment with the cartridge support 3. As shown, the firing lever 61 has a hook or notch 63 arranged to operatively receive pin 51 connected to the trigger 11. The pin 55 moved further distally as the trigger moves engages or contacts the fire lock lever 71 deflecting the lever 71.

Figure 6:
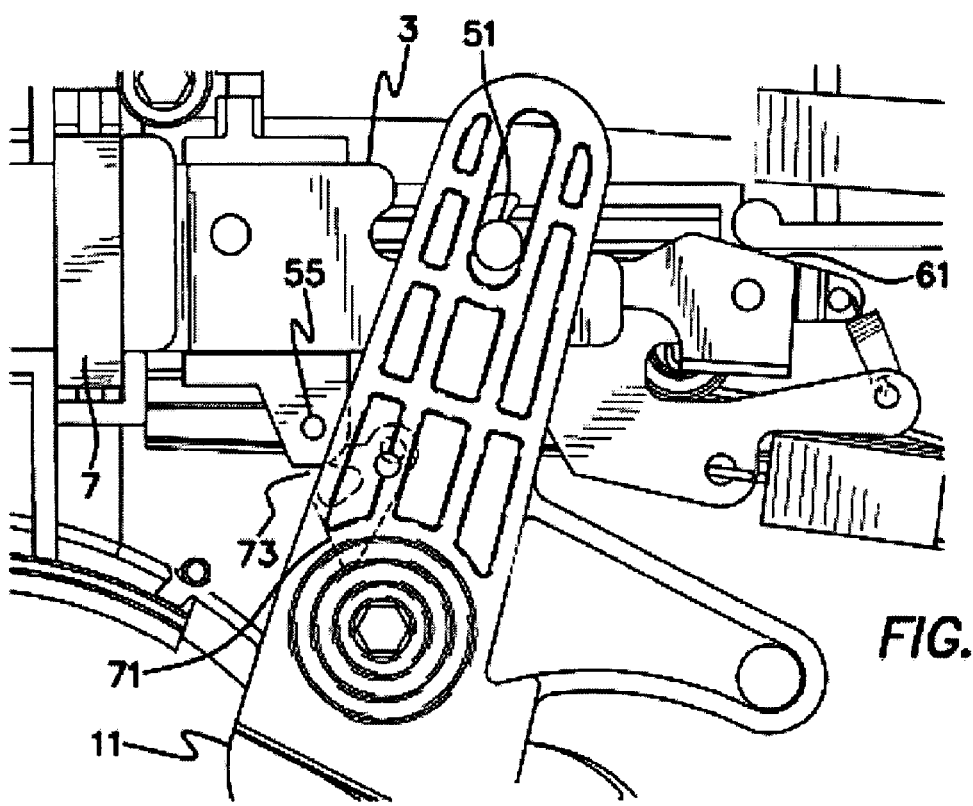

The trigger 11 is released as shown in FIG. 6, but the engagement of the latch 7 with the slot 54 in the cartridge support 3 continues to maintain the jaws 4,5 in the closed position. With the trigger released, the trigger pivots being biased by spring 11a. The pin 51 coupled to the trigger travels back proximally riding over a distal sloped surface 63b of the firing lever 61 and deflecting the firing lever 61. The firing lever 61 returns back to a horizontal or longitudinally aligned position once the pin 51 moves back sufficiently in the proximal direction, clearing the slanted, sloped or ramped surface or hook portion of the firing lever 61. The pin 55 coupled to the cartridge support 3 remains stationary and continues to contact and deflect the fire lock lever 71.

Figure 7:
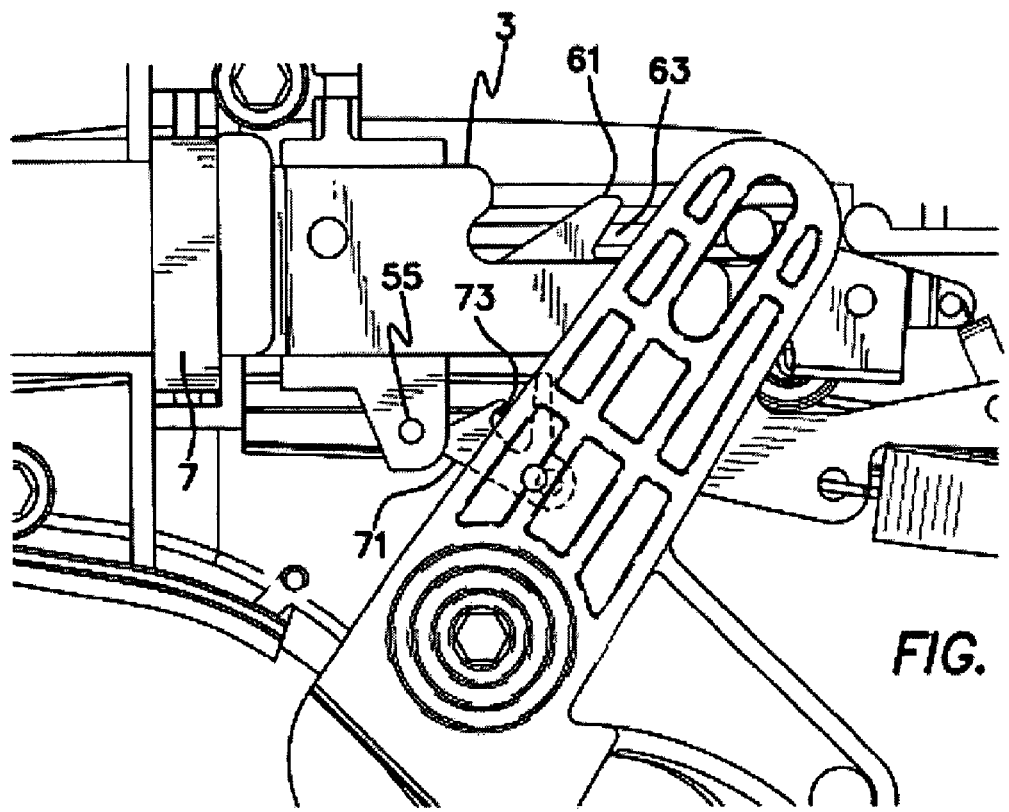

FIG. 7 shows the stapler in position to fire or eject the staples from the cartridge 6. The jaws 4,5 remain in the closed position. The pin 51 continues to travel back proximally along the firing lever 61 with the firing lever remaining in a horizontal or longitudinal position. The pin 55 remains stationary. The fire lock lever 71 moves in the proximal direction and pivots upon clearing the pin 55 allowing the fire lock lever 71 to move to a horizontal position.

Figure 8:
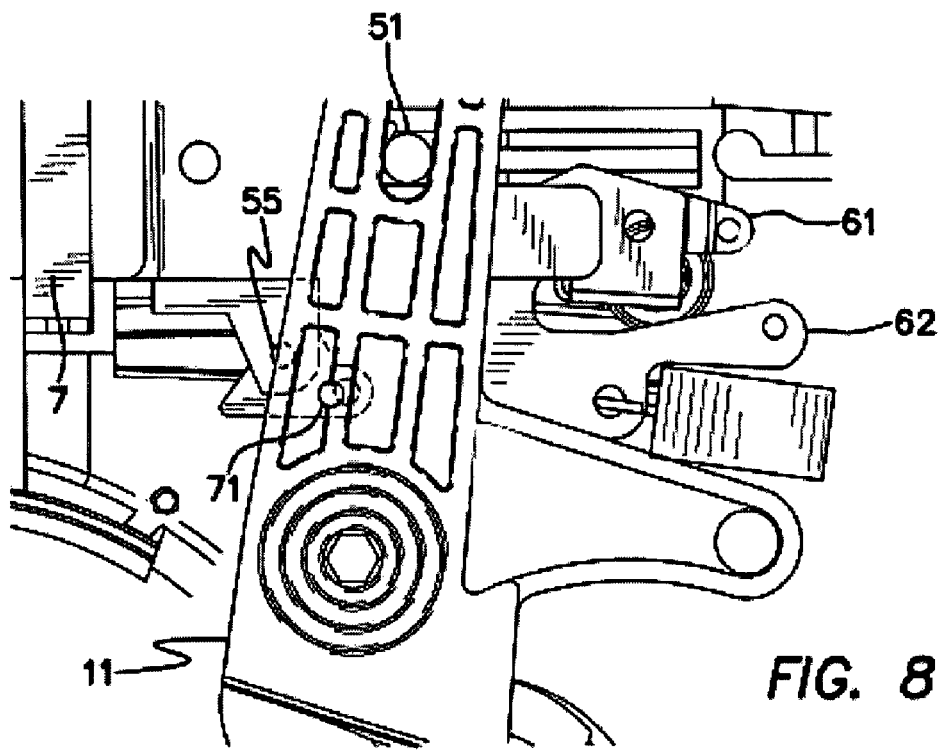

In FIG. 8, the stapler has fired or ejected the staples from the cartridge through the clamped tissue. The trigger 11 is fully closed, pulled or actuated. The engagement or contact of the surfaces or edges of latch 7 with the surfaces or edges of slot 54 in the cartridge support 3 along with the bias or force provided by the spring 91 continues to maintain the jaws in the closed position. In firing, actuating a firing stroke, the pin 51 connected to the trigger 11 moves distally to engage the notch 63 of the firing lever 61. The firing lever 61 connected to the staple pusher 14,15 causes the staple pusher to also move distally. As such, the staple pusher contacts and moves the staple drivers within the cartridge 6 subsequently ejecting the staples within the cartridge, and thus stapling the tissue clamped between the jaws 4,5.

The staple pusher 14,15 is coupled to the cartridge support 3 and as such moves as the cartridge support 3 moves. However, in one aspect, the staple pusher 14,15 has one less slot than the cartridge support 3, e.g., the staple pusher 14,15 does not have a slot that corresponds to the slot 54 on the cartridge support 3. In one aspect, the slot on the staple pusher 14,15 that corresponds to the slot 54 on the cartridge support is larger than the slot 54 in the cartridge support 3.

As such, the latch 7 maintains the position of the cartridge support 3 and the staple pusher 14,15, but the staple pusher 14,15 is allowed to move distally or towards the anvil 2. Thus, in firing, as the trigger 11 is actuated, the staple pusher 14,15 moves while the cartridge support 3 remains stationary. Also, with fewer components moving and less biasing forces tending towards the proximal direction, a tactile feedback is provided to the user indicating firing of the staples versus moving the cartridge or capturing/clamping the tissue.

The pin 55 remains stationary or fixed. In firing, the fire lock lever 71 connected to the trigger 11 moves distally to cause the lever 71 to pivot and engage the pin 55 to engage or rest within the notch 73 of the fire lock lever 71. The engagement of the fire lock lever 71 with the stationary pin 55, i.e., the pulling force of the fire lock lever 71 towards the proximal direction on the pin 55, prevents the trigger 11 from moving back distally or opening, even if the trigger is released. The locked or fixed trigger adjacent to the handle of the actuator 9 provides a visual feedback that the stapler has been fired, i.e., staples ejected.

Figure 11:
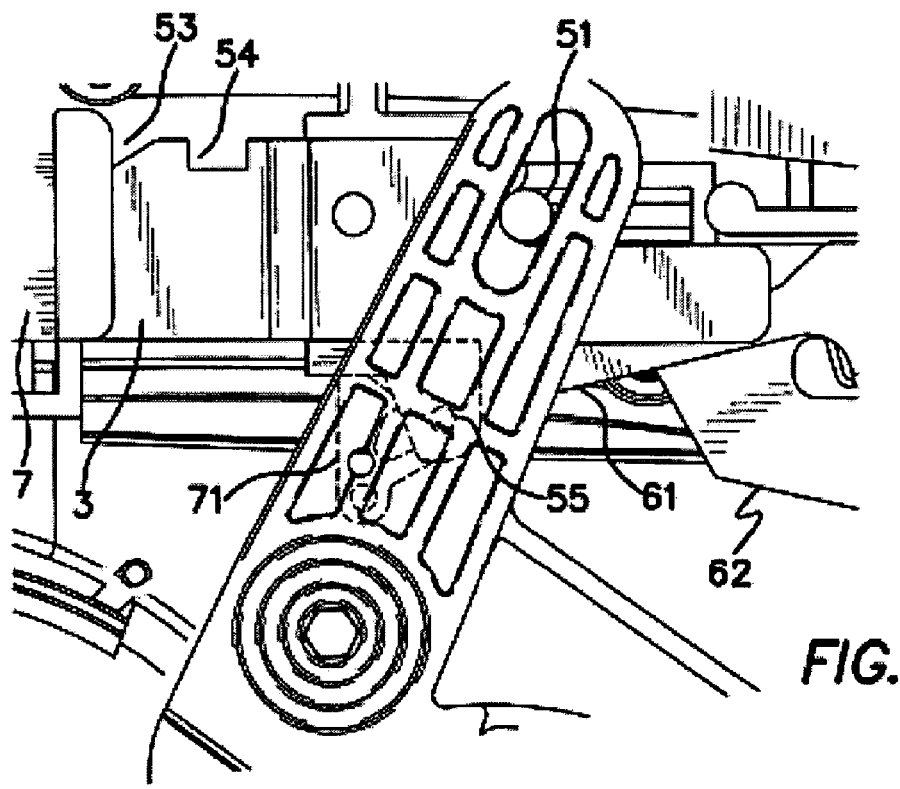
Figure 12:
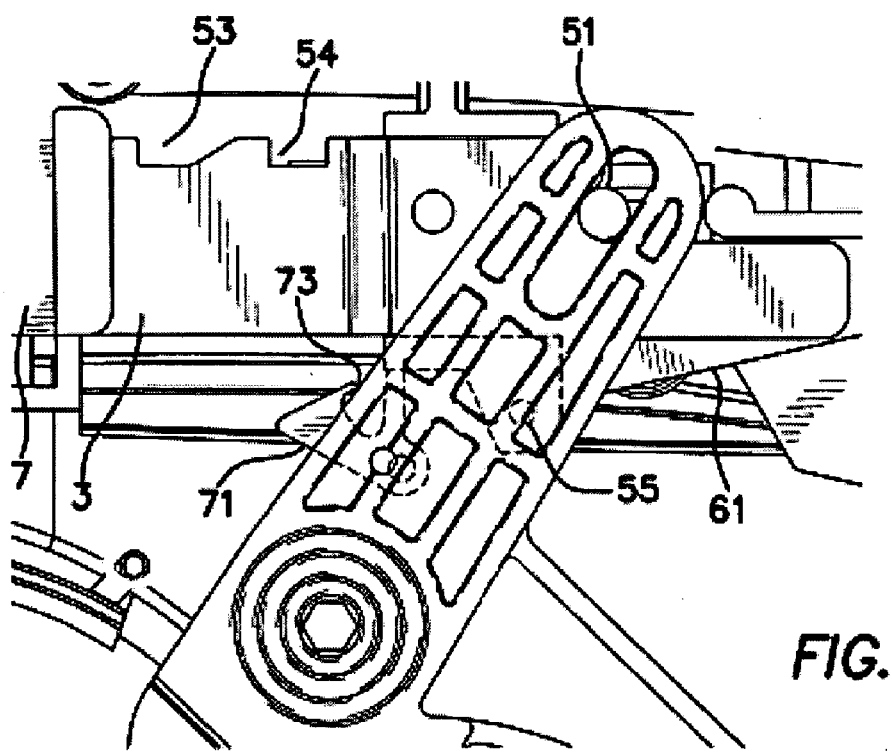
Figure 13:
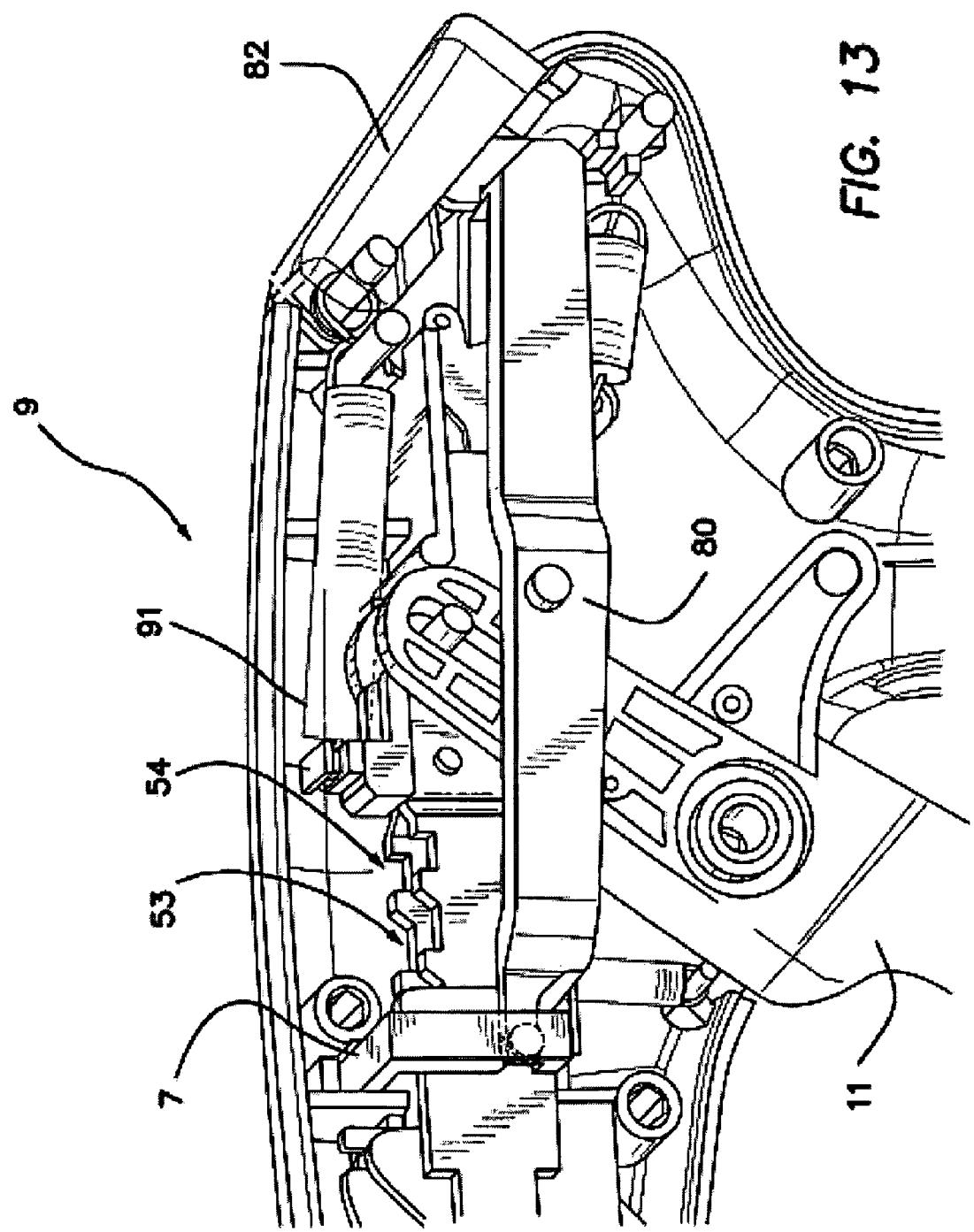
FIG. 13 is a perspective view of a surgical stapler in accordance with various aspects of the present invention.
Figure 14:
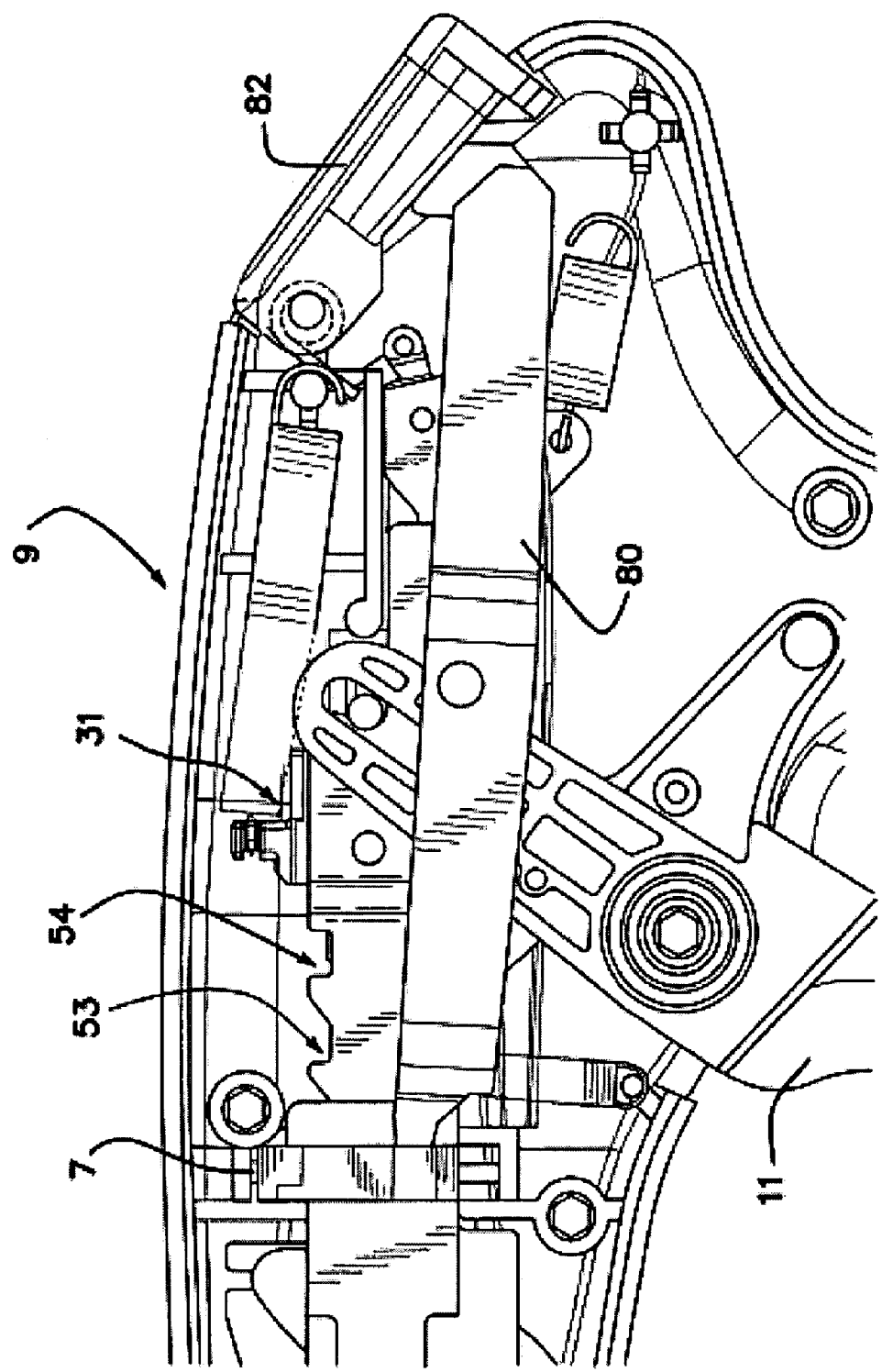
FIGS. 14-15 are side views of a surgical stapler in accordance with various aspects of the present invention.
Figure 15C:
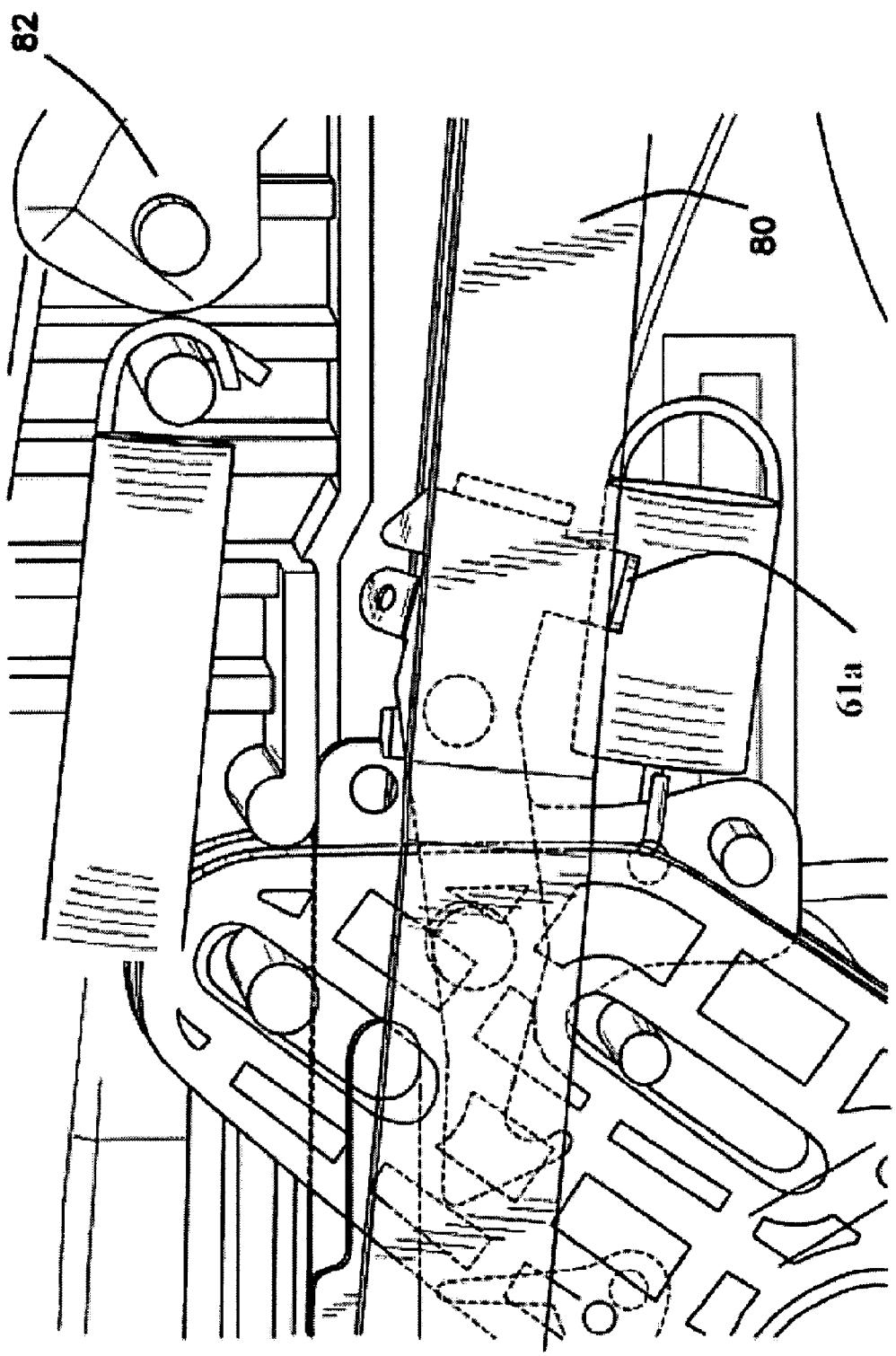
Figure 15D:
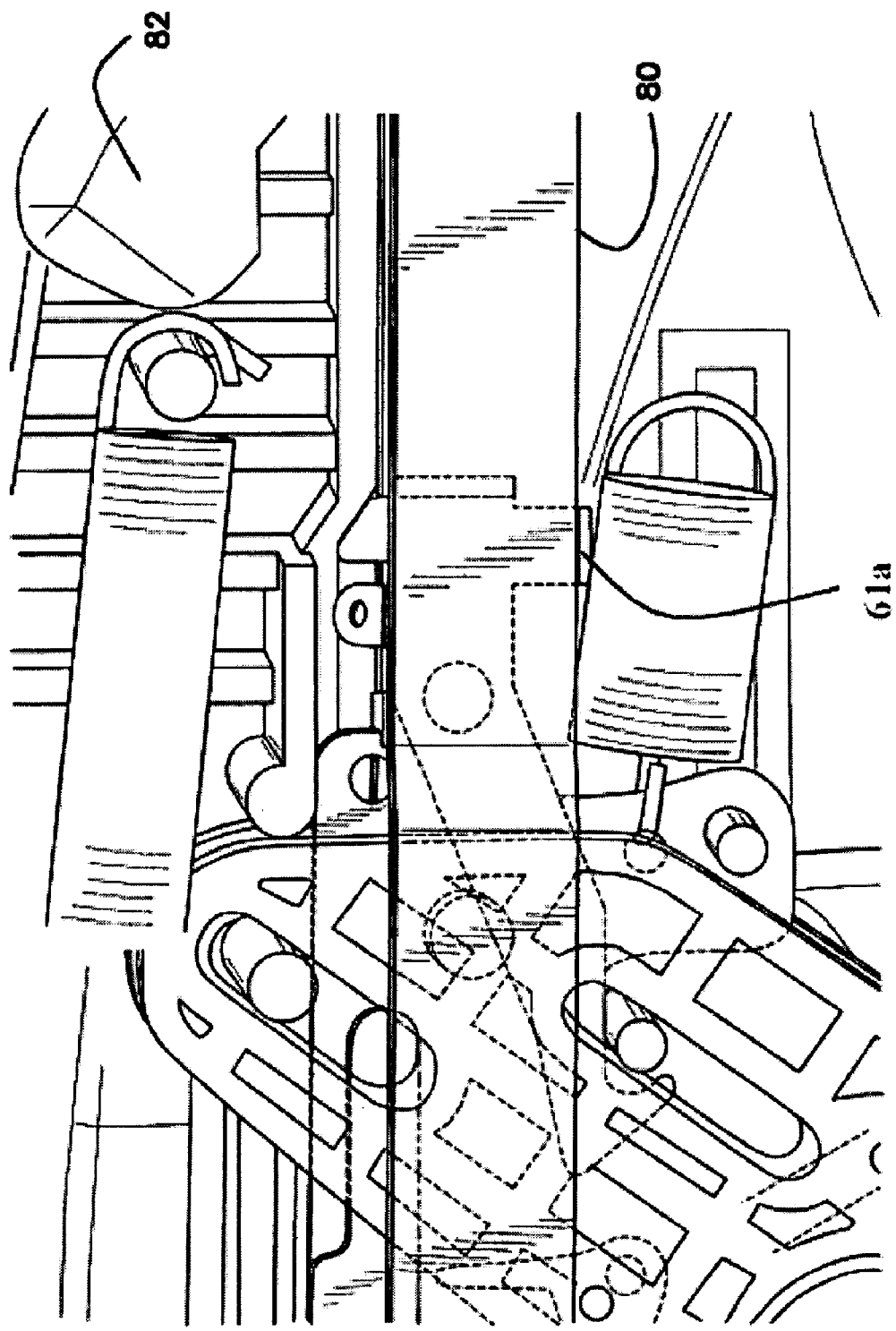

The stapler can be reset during or after the operation of the stapler. For example, upon actuation of a release button 82, the stapler is reset or moved to its original or initial open position as the jaws 4,5 move apart or open. As shown in FIGS. 9-12, the latch 7 is lifted or moved out of engagement with the slot 54 in the cartridge support 3, which allows the cartridge support 3 to retract proximally. The latch 7 is connected to a release latch or arms 80 that is coupled to a release button 82 on the actuator 9 (FIGS. 13-14). In one aspect, with the button 82 actuated or pressed, arms 81 of the release latch 80 pivot and lift or move the latch 7 out of engagement with the cartridge support 3. The button 82 in one aspect is biased away from the actuator by a leaf spring 95 coupled to the actuator. In one aspect, the release arms 80 and latch 7 are biased to engage the cartridge support 3 by a compression spring 96 coupled to the actuator 9.

Figure 9:
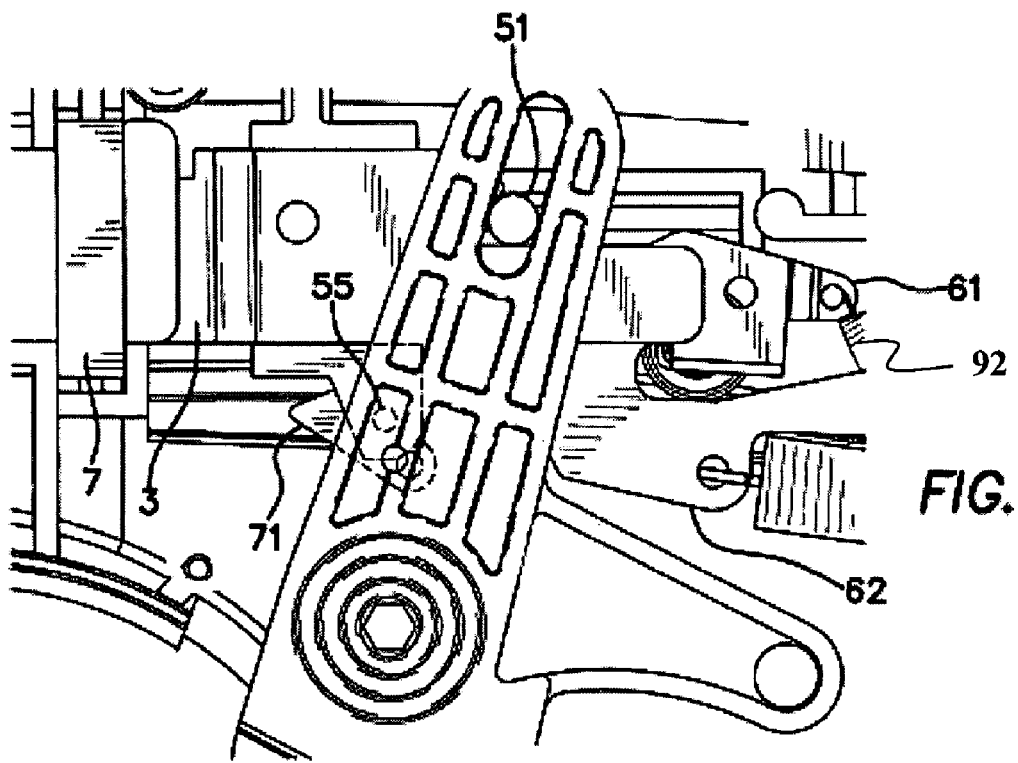
Figure 10:
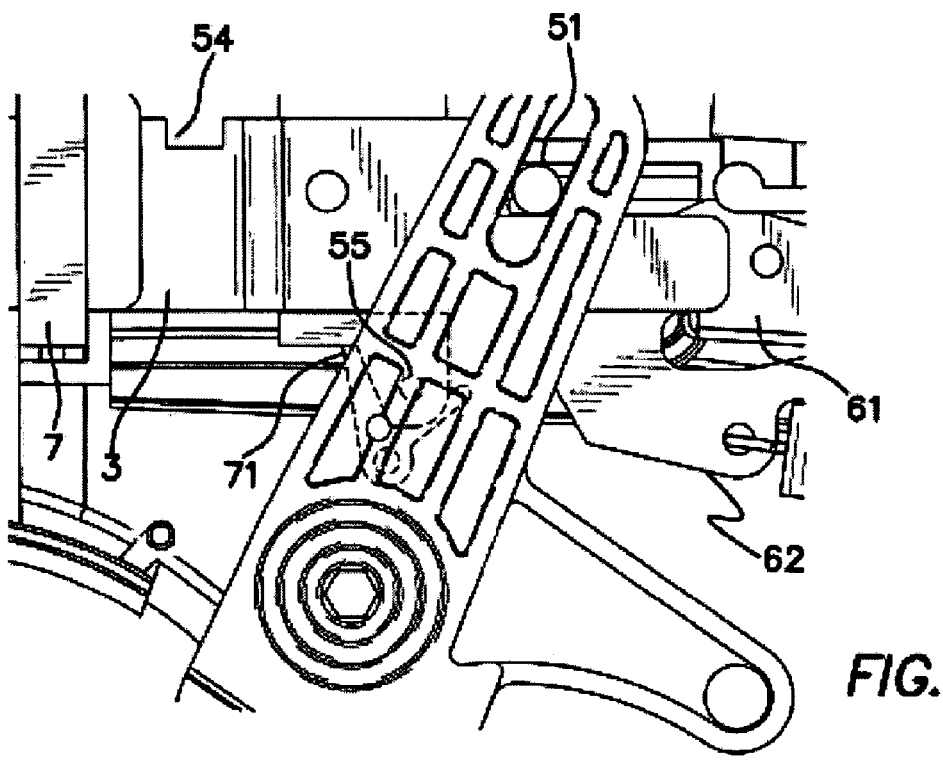

The firing lever 61 remains in the horizontal position, but is eventually deflected as shown in FIGS. 9-10. With the cartridge support 3 retracting, being urged by spring 91, the pin 55 also starts to or is allowed to move proximally causing the fire lock lever 71 to start to pivot. Also, with the pin 55 moving, the engagement of the fire lock lever 71 with the pin 55 starts to be released. Fire lock lever 71 and pin 55 typically interact to prevent the trigger from moving back distally or opening, even if the trigger is released. However, with the fire lock lever 71 disengaged from pin 55 the trigger is now allowed to open. The cartridge support 3 retracting also engages pin 51 to further cause the trigger to open (FIG. 11). FIG. 12 shows the stapler moved back to the original default or initial open position.

FIGS. 15A-D show an actuator 9 in accordance with various aspects of the present invention. The trigger 11 of the actuator 9 is used to advance the cartridge and fire staples from the cartridge 6. A release button 82 is also coupled to the actuator and is configured to reset the stapler back to its initial opened position at any time throughout operation of the stapler. As the trigger 11 is first actuated, the cartridge support 3 with the cartridge 6 and the staple member or pusher 14,15 advance towards the anvil 2. When the trigger 11 is fully actuated, the cartridge 6 is positioned at a specific distance to form staples against the anvil 2. Also, after the trigger 11 is released, the trigger engages the firing lever 61'. When the trigger 11 is actuated again, the firing lever connected the staple pusher 14,15 advances to eject the staples from the cartridge 6.

As previously noted, actuating the release button 82 can occur throughout the operation of the stapler. For example, as the stapler is ready to fire staples, e.g., after the first actuation of the trigger, the release button can be actuated. Since the firing lever 61' is already engaged or capable of being engaged by the trigger 11, a biasing mechanism 61a is provided to ensure that the firing lever is disengaged by the trigger irrespective of movement of the cartridge supports or staple or firing pusher 14,15. A protrusion or tab, in one aspect, provides the biasing mechanism. The tab extends from the firing lever 61' to ensure engagement with the release latch or arms 80 coupled to the release button 82 to bias the firing lever 61' directly when the release button is actuated. As such, activation of the button moves the release arms 80 that contact the tab 61a from the firing lever 61' disengaging the firing lever from pin 50.

Figure 16:
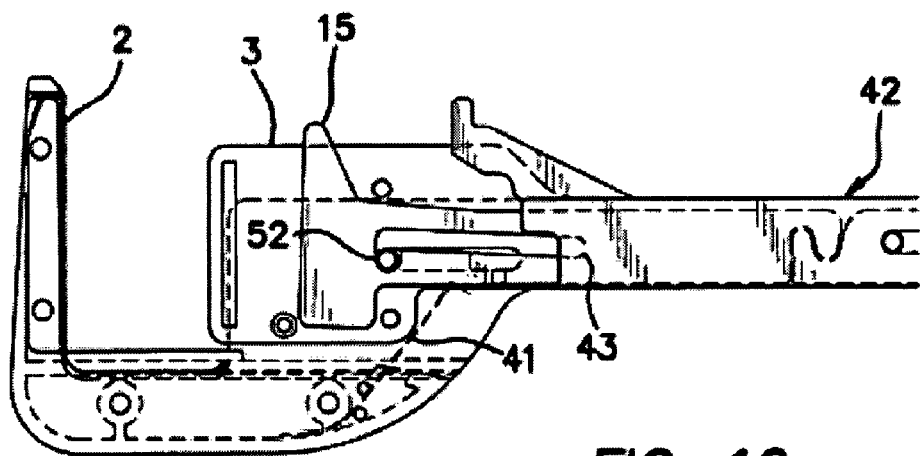
FIGS. 16-22 are side views of a surgical stapler in accordance with various aspects of the present invention.

In one aspect, a lockout mechanism is provided to prevent re-firing of a spent staple cartridge and re-clamping of tissue through interaction with a firing member and the disposable staple cartridge. Referring to FIG. 16, the stapler is shown without a loaded disposable cartridge 6. In this state, the staple pusher 14,15 pivots upward due to a biasing member 41, e.g., a spring, located in the frame of the stapler. The staple pusher in one aspect comprises a two-piece elongate structure, a proximal portion 14 and a distal portion 15. The proximal and distal portions of the staple pusher are connected at a mating connection or hooks 42. The mating hooks 42 allows the distal portion 15 of the staple pusher being biased by the spring 41 to pivot relative to the proximal portion 14 of the staple pusher. A projection, post or pin 52 disposed on the cartridge support 3 extends across a channel formed between the cartridge support 3 through which the staple pusher slides. The pin 52 extends through a generally L-shaped slot 43 in the staple pusher 15. The pin 52 attached or the cartridge support 3 moves with the cartridge support 3. The engagement of pin 52 with the bottom or L-portion of the L-shaped slot prevents the staple pusher 14,15 from being moved towards the anvil 2. With the staple pusher being immobilized or otherwise prevented from moving, the cartridge support 3 movements are also restricted. Operationally, from the default initial open position to the closed or clamped position, the staple pusher 14,15 and cartridge support 3 movements are coupled to each other. As such, movement of the trigger 11 of actuator 9 causes movement of both the staple pusher 14,15 and cartridge support 3 away from the actuator 9 toward the anvil 2. The engagement of the pin 52 with the bottom portion of the L-shaped slot 43 in the staple pusher 14,15 also limits the distance or movement of the staple pusher being biased out of the stapler by spring 41.

Figure 17A:
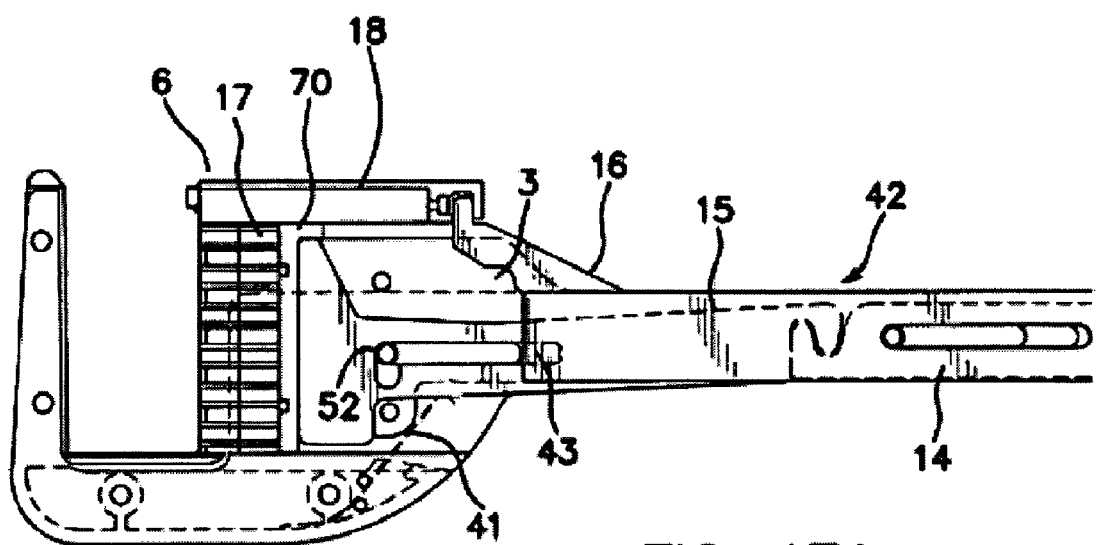
Figure 17B:
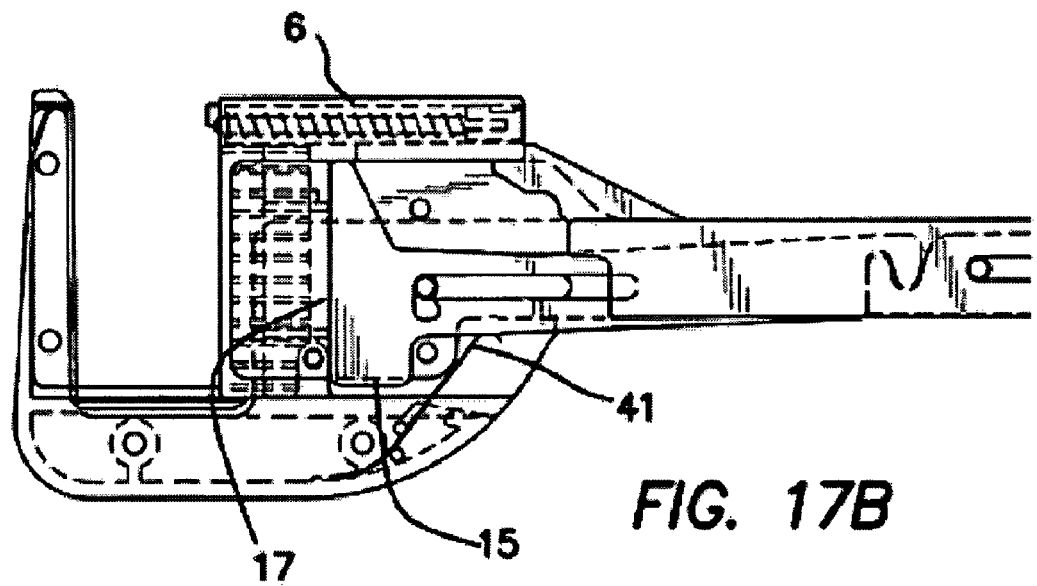

In FIG. 17A-B, the stapler is in an open or initial position and loaded with a staple filled or loaded cartridge 6. The staple driver(s) 17 disposed or included with the cartridge 6 that facilitate ejection or firing of the staples from the cartridge when contacted by the staple pusher 14,15. A portion of the staple driver(s), e.g., projection 70, engages the distal portion of the staple pusher deflecting or biasing the staple pusher downward against or counteracting the force of spring 41. This deflection also moves the bottom portion of the L-shaped slot 43 in staple pusher 14 substantially out of contact with pin 52. Thus, the staple pusher becomes unobstructed and free to move.

Figure 18:
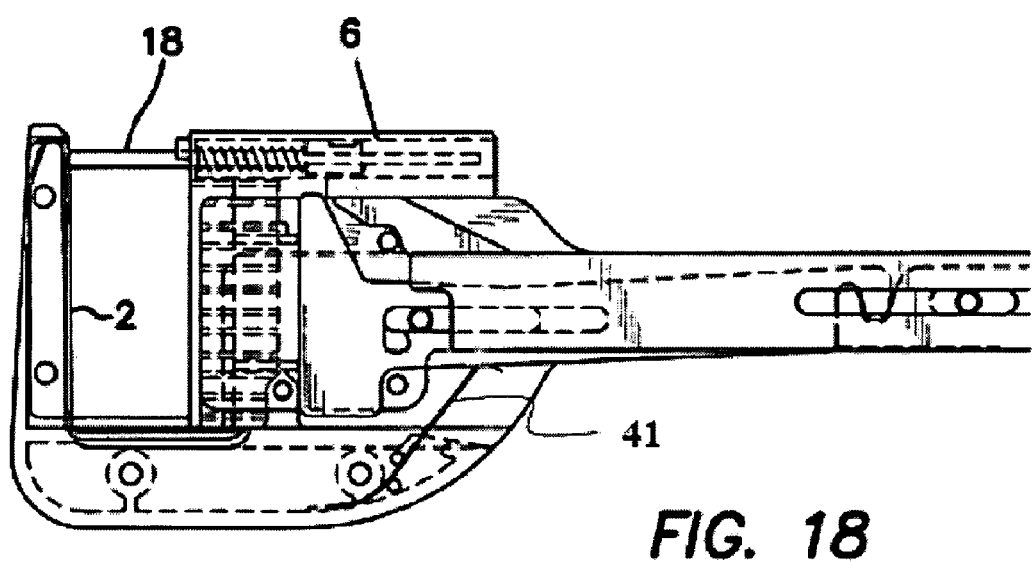
Figure 19:
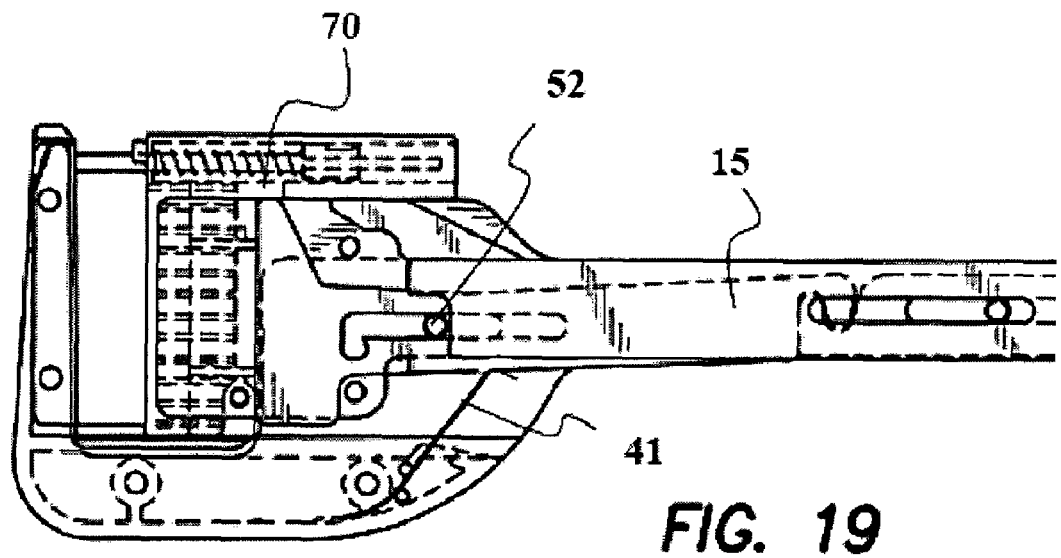
Figure 20:
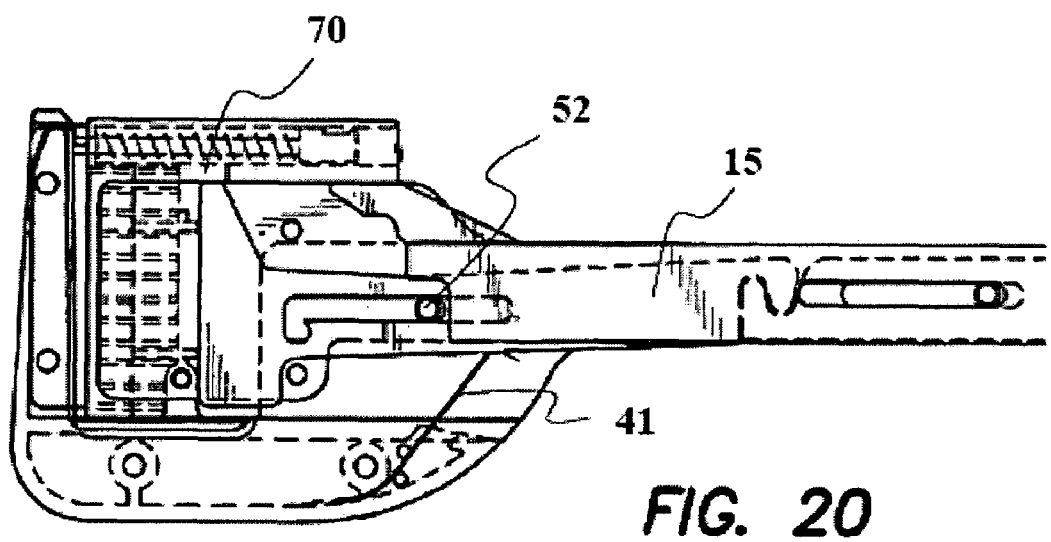
Figure 21:
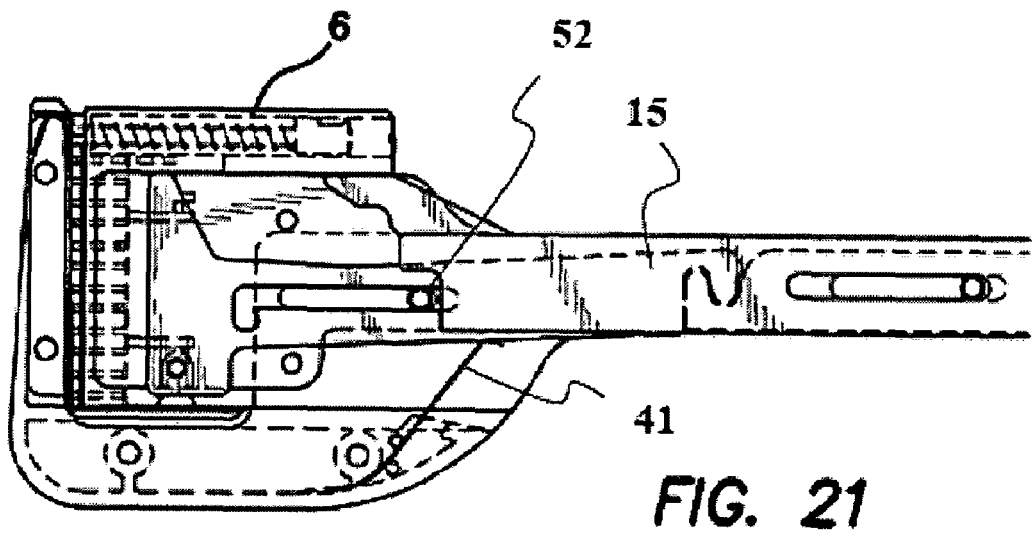

The stapler, in FIG. 18, is in the next stage of actuation or in the capture position with the capture pin advanced and the cartridge 6 moved towards the anvil 2. FIG. 19 shows the stapler being partially closed and FIG. 20 shows the stapler closed (tissue clamped). FIG. 21 shows the staples fired from the cartridge 6.

Figure 22:
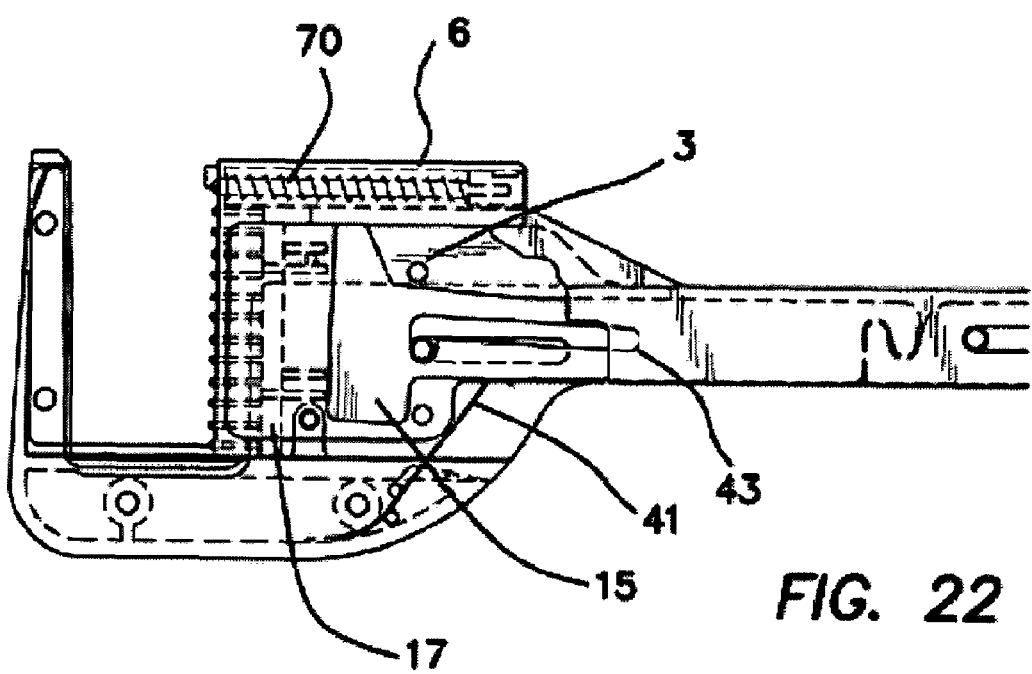

FIG. 22 shows the stapler opened or reset to allow removal of the stapler from the operation site or tissue. With the staple drivers 17 and thus projection 70 in their most distal position in the cartridge 6, the staple pusher 14,15 is permitted to pivot upward due to spring 41. Thus, the pin 52 engages the bottom portion of the L-shaped slot in the staple pusher 15, which prevents further distal movement of the staple pusher 14,15 and also cartridge support 3. Hence, re-firing of a spent or empty staple cartridge and re-clamping of tissue, i.e., preventing jaw closure, are prevented until a loaded cartridge is inserted between the cartridge support.

Figure 23:
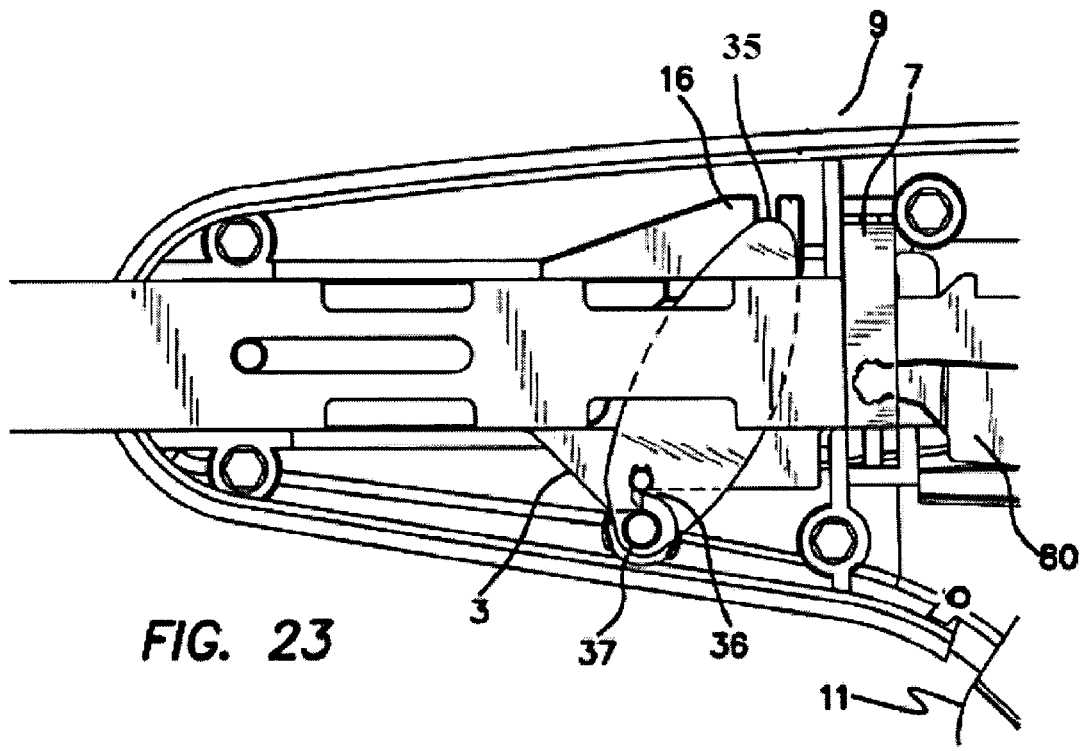
FIGS. 23-26 are side views of a surgical stapler in accordance with various aspects of the present invention.

As previously described and shown in the preceding figures, the capture pin 18 within cartridge 6 is operatively connected to the capture pin pusher or driver 16. In one aspect, as shown in FIG. 23, the capture pin pusher 16 has a slot 35 on one end, e.g., the proximal end, in which a pin or post extending from a pivot lever 34 connects the pivot lever 34 to the capture pin pusher 16. In the default or open position, a pin, detent or post 37 extending from the other end of the pivot lever 34 is operatively coupled to the cartridge support 3 via a slot 36 in the cartridge support 3. As shown in FIG. 23, the pin 37 extends from the lever and rests in the slot 36.

Figure 24:
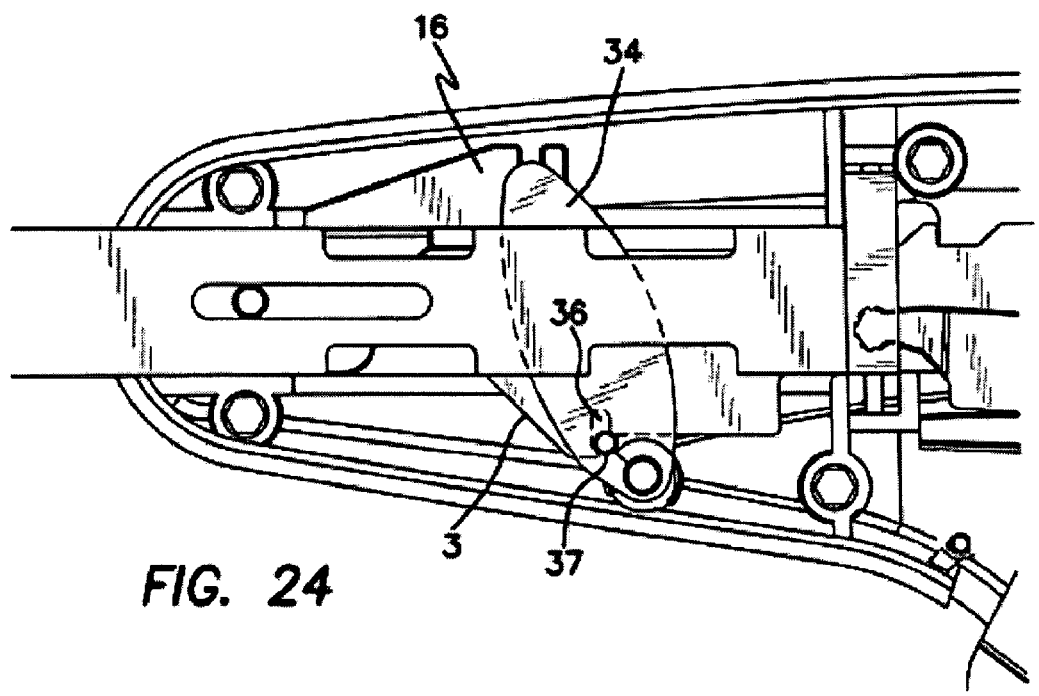
Figure 25:
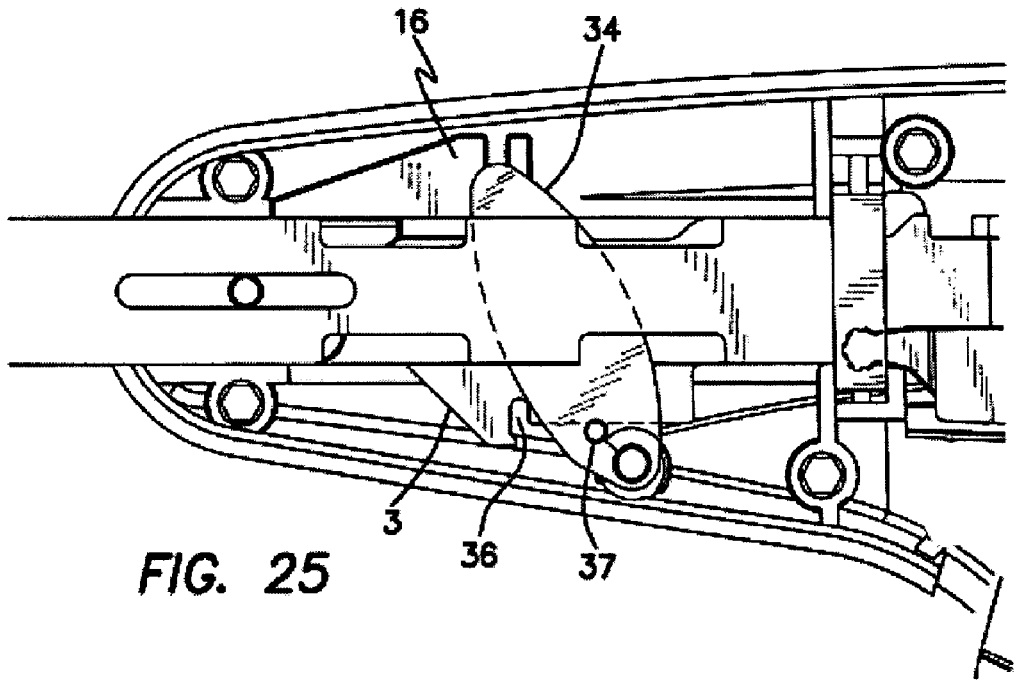
Figure 26:
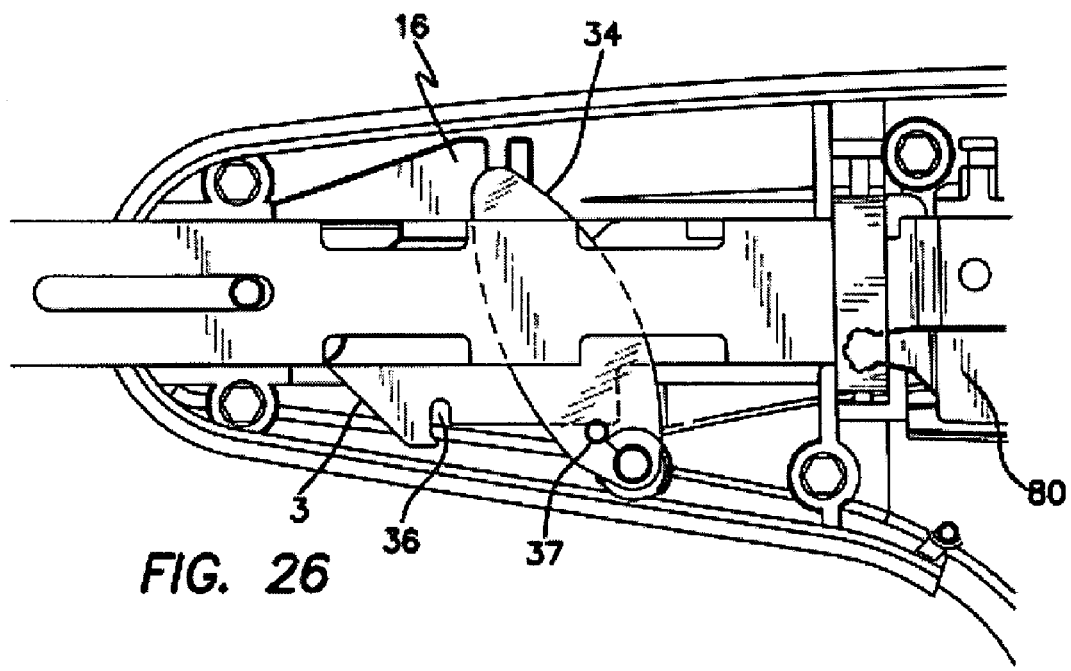

Movement of the trigger 11 of the actuator 9 causes the cartridge support 3 to move longitudinally as post 51 is moved by trigger 11. With the cartridge support 3 moving, the slot 36 in the cartridge support 3 interacts with the pin 37 of lever 34 causing the lever 34 to pivot in a counter-clockwise direction. Continued movement of lever 34 causes pin 37 to move out of the slot 36 (FIG. 24). The counter-clockwise motion of the lever 34 causes the capture pin pusher 16 via the interaction with the pin from lever 34 with the slot 35 in the capture pin pusher 16 to advance or move longitudinally, which in turn extends the capture pin 18 into the anvil 2 of jaw 4 capturing tissue within the space defined by the jaws/frame and capture pin. As shown in FIG. 25, the pin 37 rides along a surface of the cartridge support 3 as the cartridge support 3 is advanced distally to partially close the jaws. In and to the closed or clamped position of the stapler, as shown in FIG. 26, the pin 37 continues to slide along the surface of the cartridge support 3.

In FIG. 27, the stapler is in the open or initial position with a loaded cartridge, i.e., a cartridge having staples. In this position, the jaw 5 is allowed to move freely and staples may be fired. A lever 21 is pivotally connected to the cartridge support 3 via a rivet, pin or post 22. The lever 21 has a tip 23 that contacts a portion of the staple drivers or a protrusion 26 extending from the staple drivers to maintain a substantially horizontal position. The other end of the lever 21 has a pin 24 extending through an aperture 25 within the frame 10. The pin 24 slides along the aperture 25 as the cartridge support 3 is moved. Trigger 11 of actuator 9 is in an open position.

Figure 29A:
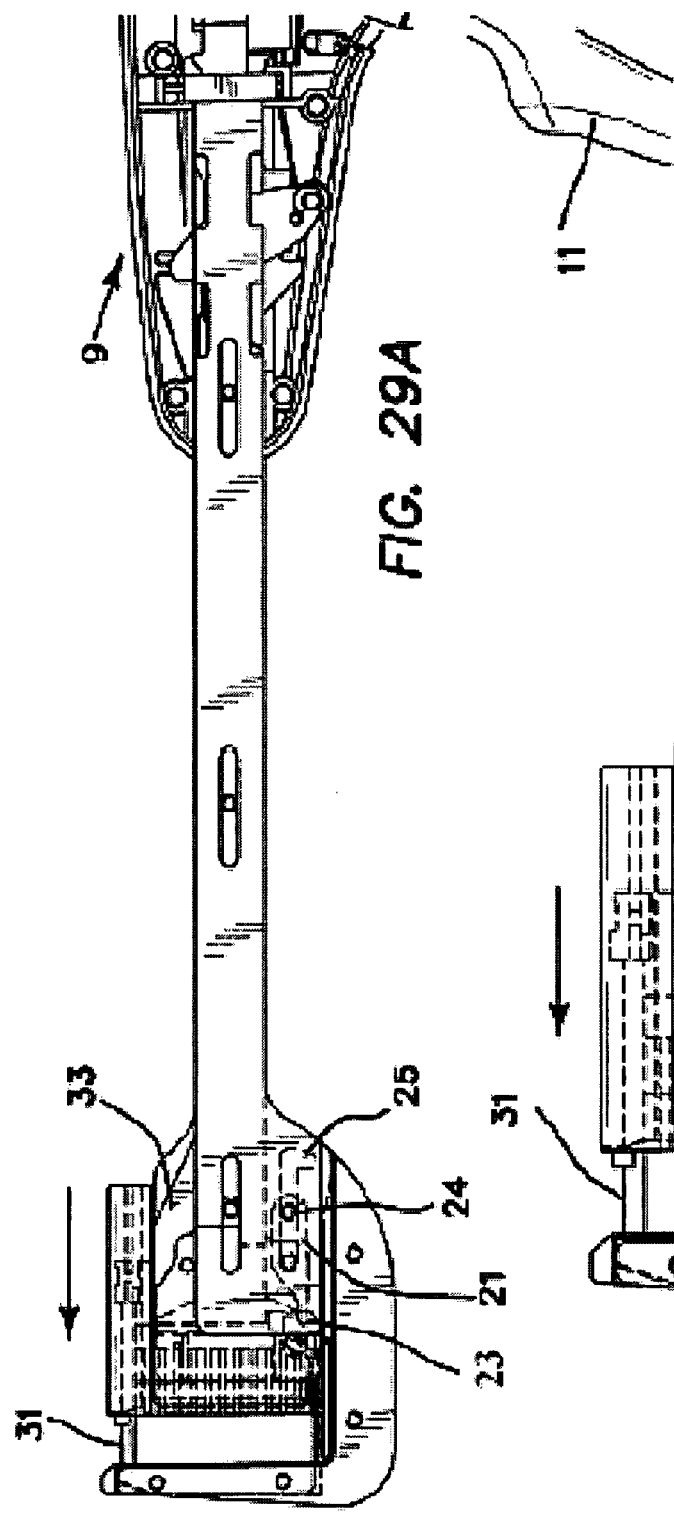
Figure 29B:
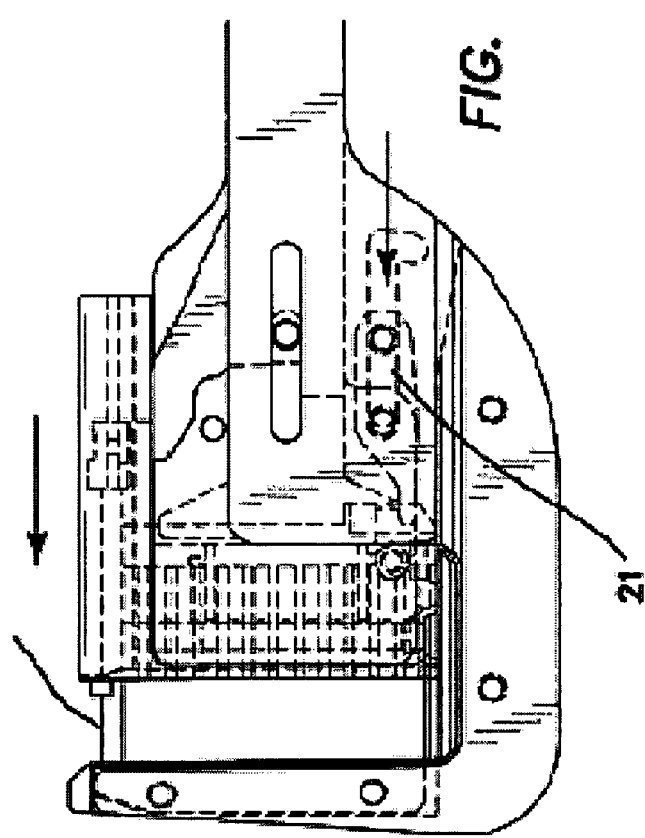
Figure 30A:
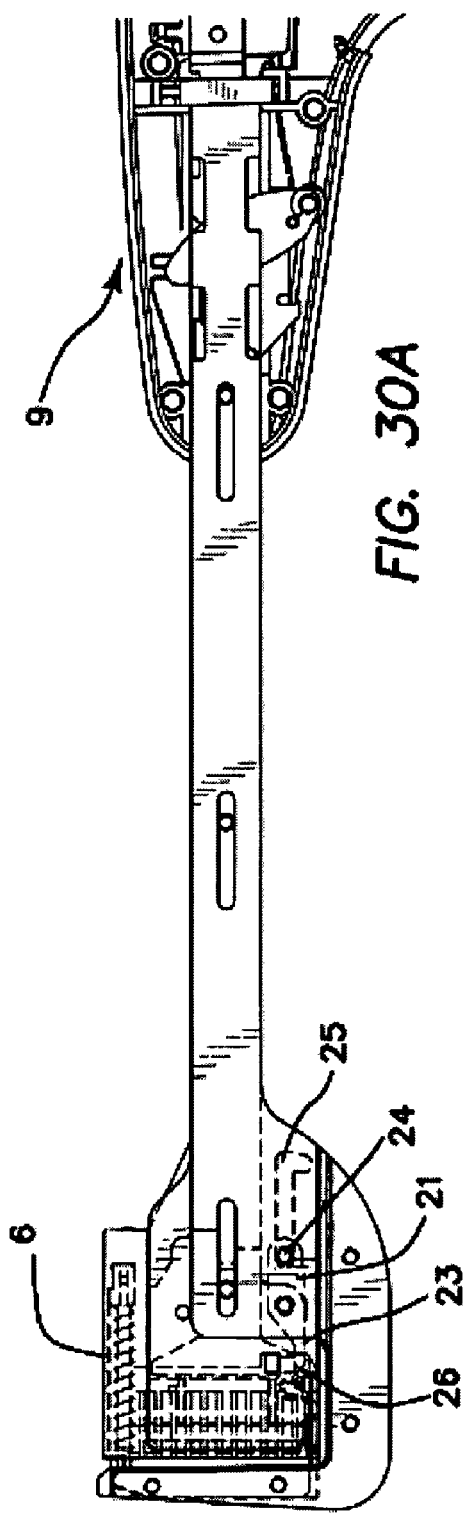
Figure 30B:
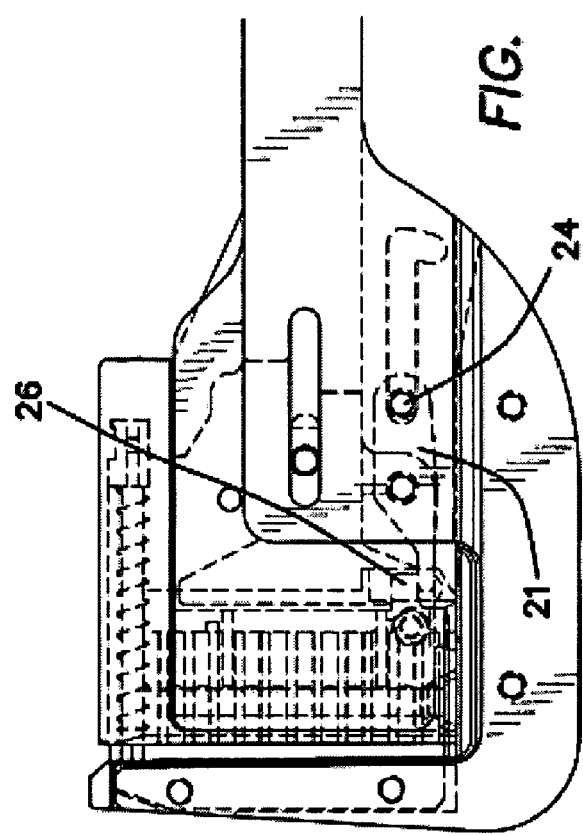

FIGS. 28A-B show the pin 24 sliding along the aperture 25 slightly and the lever 21 and tip 23 remaining substantially horizontal as the capture pin 31 driven by capture pin pusher 33 is extended into the anvil. Trigger 11 of actuator 9 and the jaws 4,5 are moved to a capture position. FIGS. 29A-B show the pin 24 continuing to slide along the aperture 25 and the lever 21 and tip 23 remaining substantially horizontal as the stapler continues to close. Trigger 11 of actuator 9 and the jaws 4,5 are moved to a partially closed position. FIGS. 30A-B show the pin 24 slide into the end of the aperture 25 and the lever 21 and tip 23 remaining substantially horizontal as the stapler is closed, clamping tissue between the jaws. Trigger 11 of actuator 9 and the jaws 4,5 are moved to a closed position.

FIG. 31 shows that the pin 24, lever 21 and tip 23 remain in the same position as the stapler is prepared to fire staples and the trigger 11 is moved back to an open position. FIGS. 32A-B show the pin 24, lever 21 and tip 23 remain in the same position as the stapler is fired and staples are ejected from the cartridge 6 with the trigger 11 moved back to a closed position. In this position, the protrusion 26 extending from the staple drivers moves with the staple drivers as the staples are fired and thus no longer contacts the tip 23 of lever 21. Thus, the aperture 25 within frame 10 contacting pin 24 maintains the lever 21 in a substantially horizontal position.

After firing, the stapler is reset in which the capture pin 31 and jaws 4,5 retract. As the cartridge support 3 retracts, the pin 24 slides along the aperture 25 until it reaches the proximal end of the aperture 25 where it is allowed to pivot. FIGS. 33A-B show the lever 21 pivoted, i.e., no longer in a horizontal position, with pin 24 moved in a lower part of an L-shaped portion of the aperture 25 of the cartridge support 3. The contact of pin 24 with the aperture 25 prevents longitudinal movement of the cartridge support even if the trigger 11 is actuated.

Figure 34:
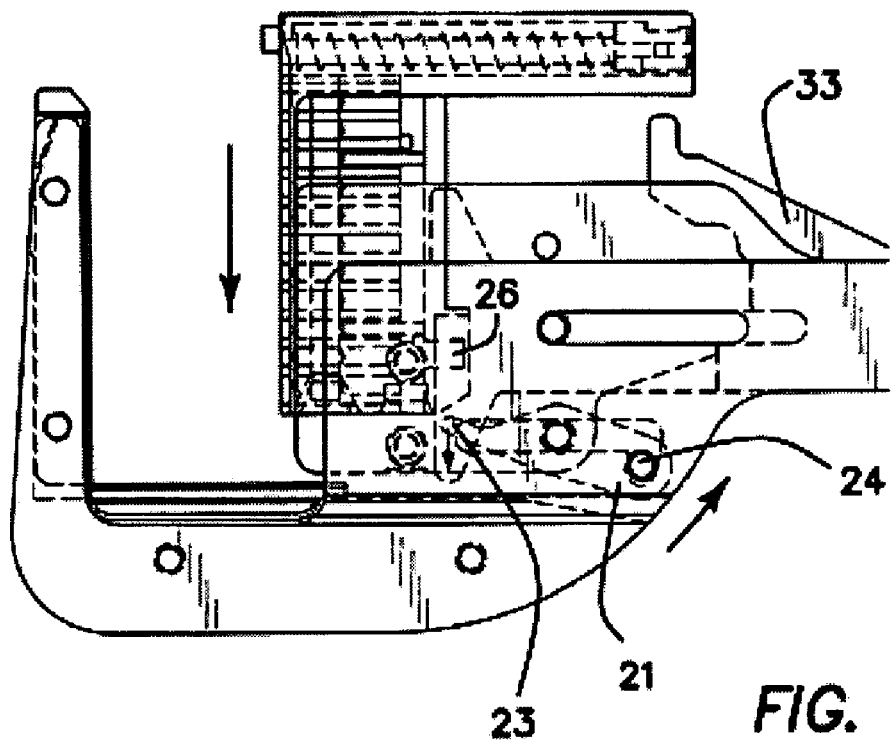
Figure 35:
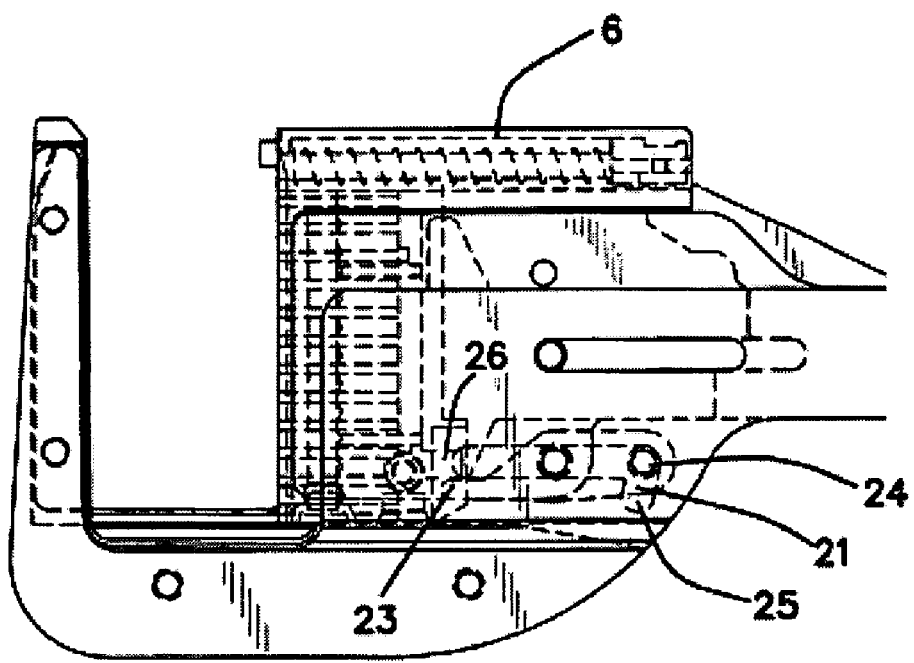

As shown in FIG. 34, when a loaded cartridge is inserted into the cartridge support 3, the protrusion 26 contacts tip 23 of lever 21 to causing the lever 21 to rotate and pin 24 to move out of the lower part of the aperture 25 placing lever 21 in a horizontal position (FIG. 35). In this position, the jaw 5 is allowed to move freely and staples within the cartridge 6 may be fired.

Figure 36:
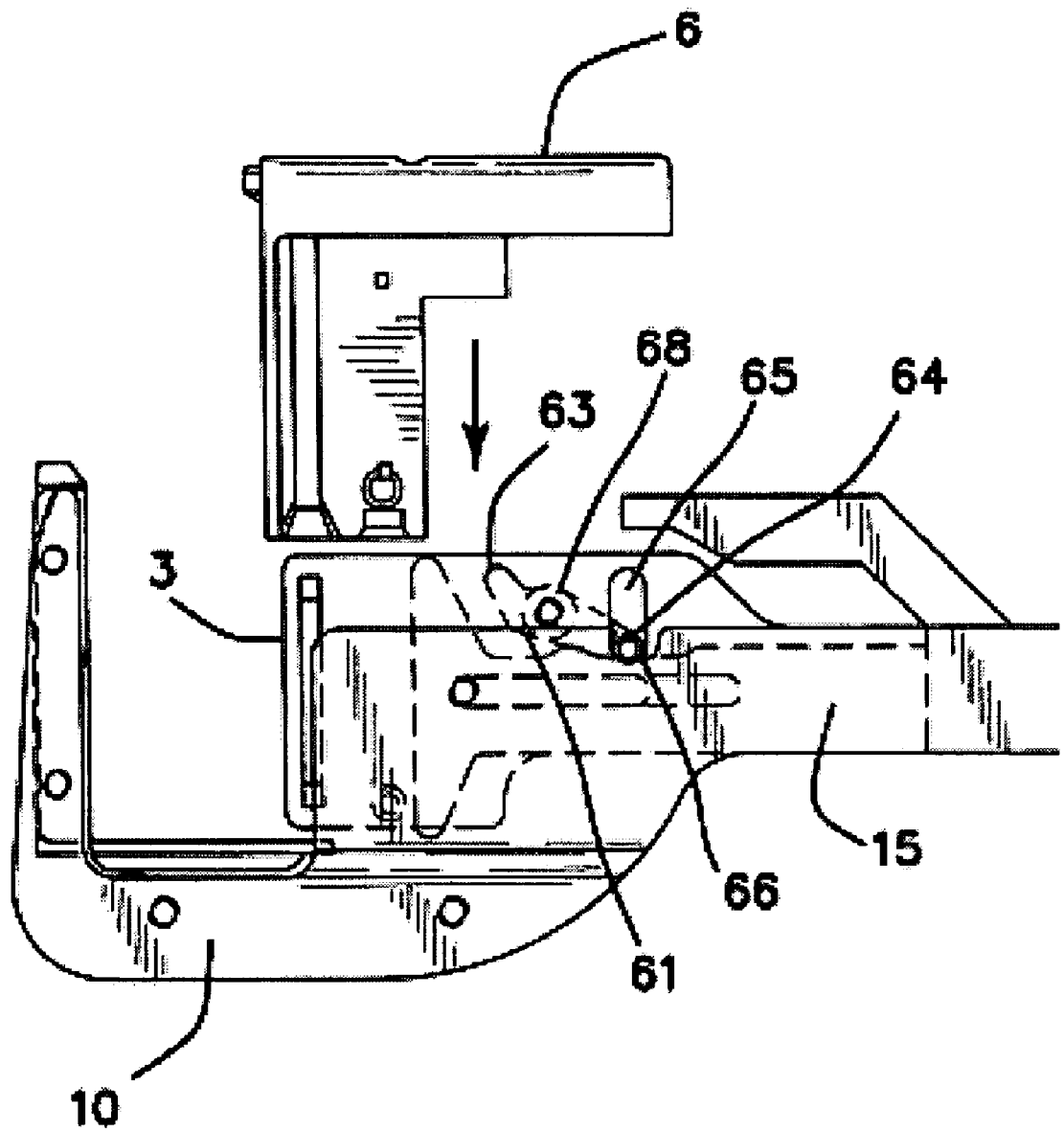
FIGS. 36-44 are side views of a surgical stapler in accordance with various aspects of the present invention.
Figure 37:
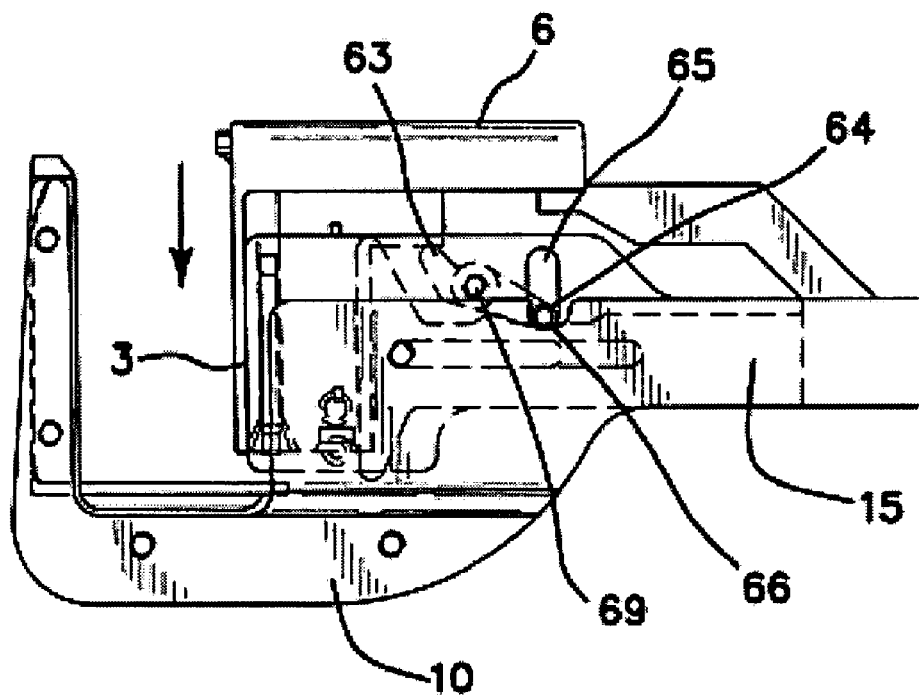
Figure 38:
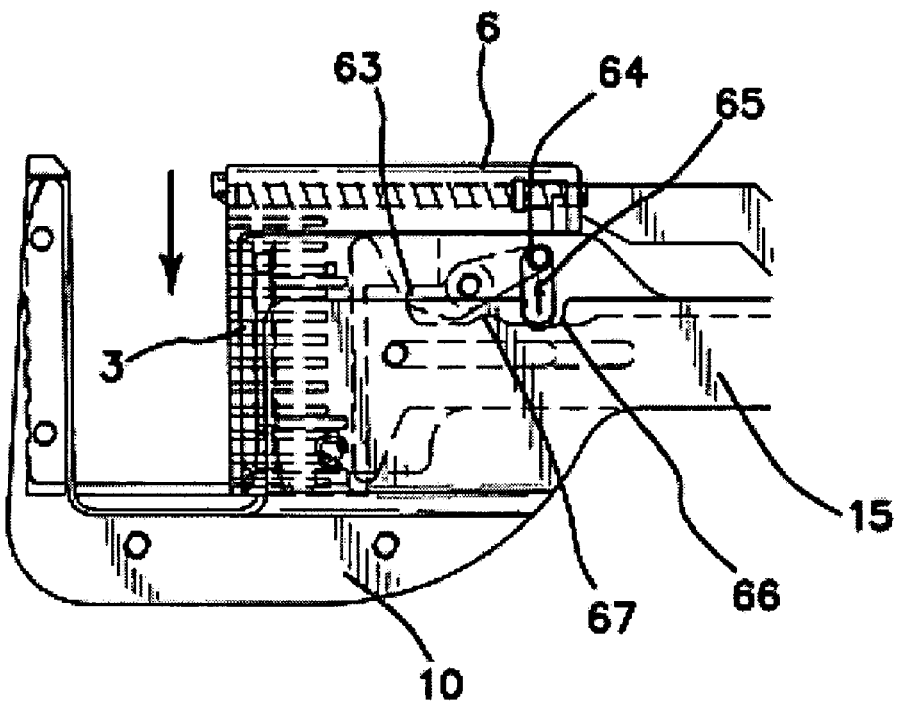
Figure 39:
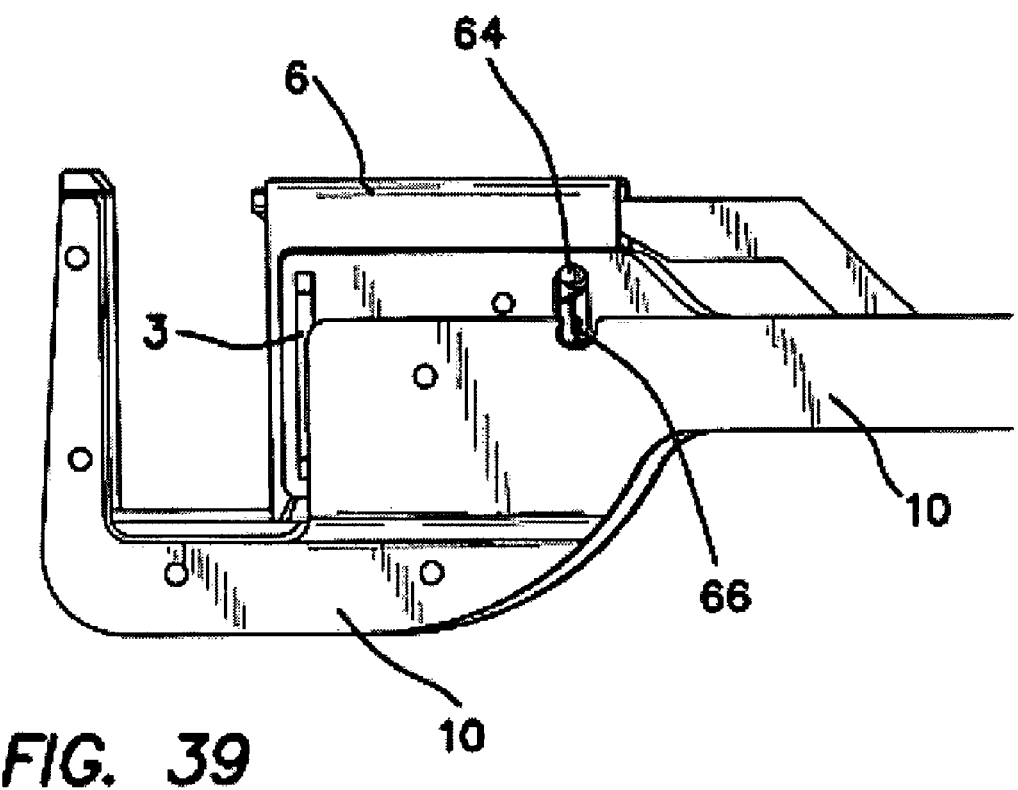

In FIG. 36, the stapler is in the open or initial position with a cartridge 6 being loaded into the stapler. In this position, the jaw 5 is not allowed to move freely and staples may not be fired. A pivotally connected lever 61 is connected to the cartridge support 3 via a rivet, pin or post 68. Without a cartridge loaded into the stapler, the lever 61 prevents movement of the jaws 5. A pin 64 extends from one end of the lever 61. The pin 64 extends through an aperture 65 of the cartridge support 3 and rests in a slot 66 of frame 10. As such, the pin 64 interacting with the cartridge support 3 and frame 10 prevents approximation of the jaw 5. In FIGS. 37-39, with a cartridge being loaded into the stapler, tip 63 of the lever 61 contacts a portion or protrusion (not shown) of the staple drivers or cartridge 6 causing rotation of the lever 61. As such, the pin 64 slides along the aperture 65 and out of the slot 66 of frame 10.

Figure 40:
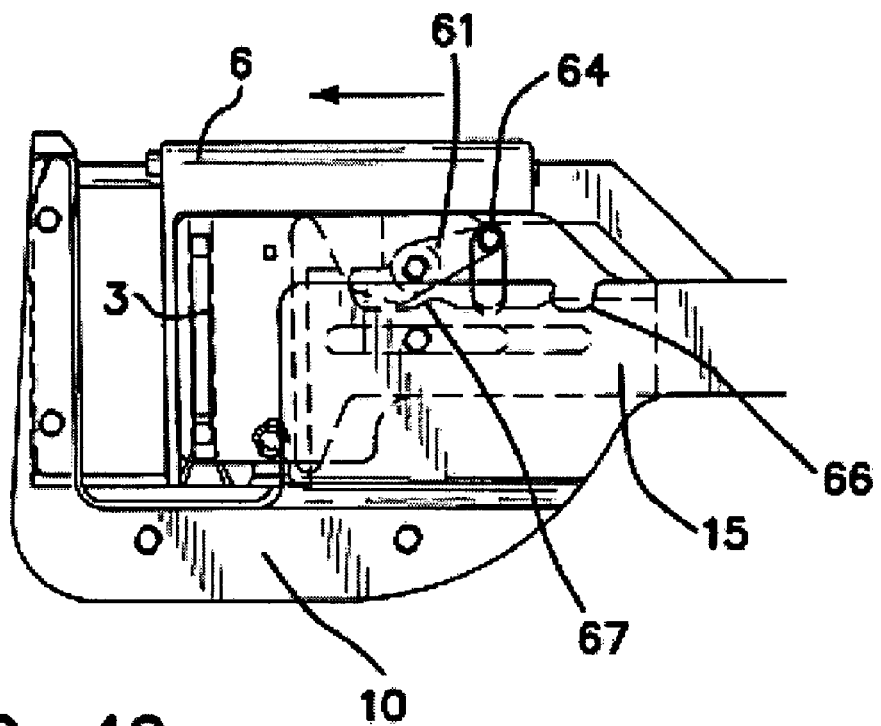
Figure 41:
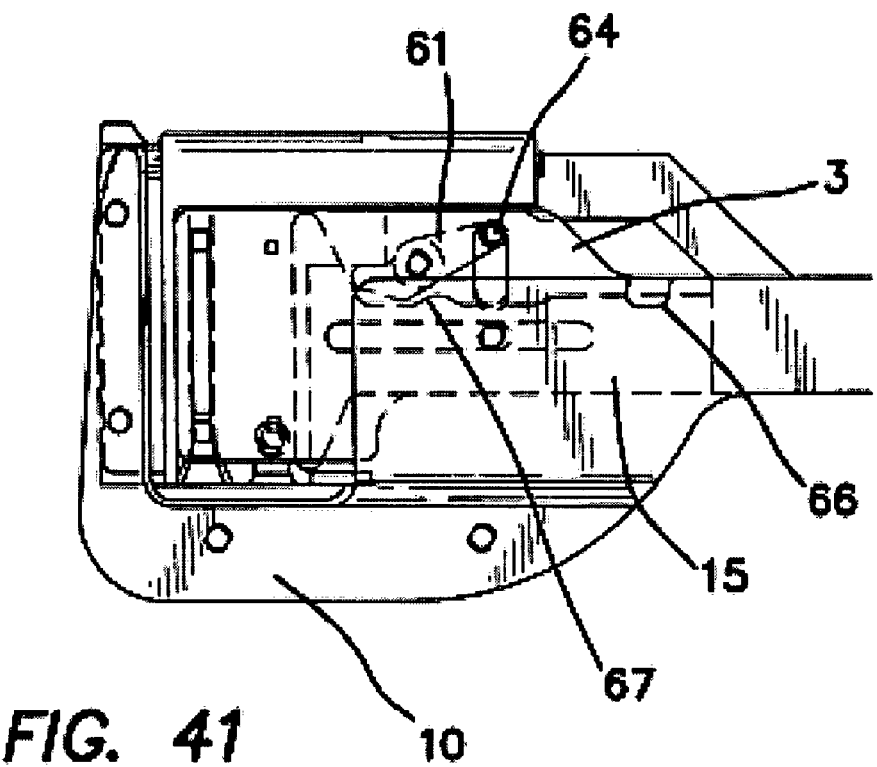
Figure 42:
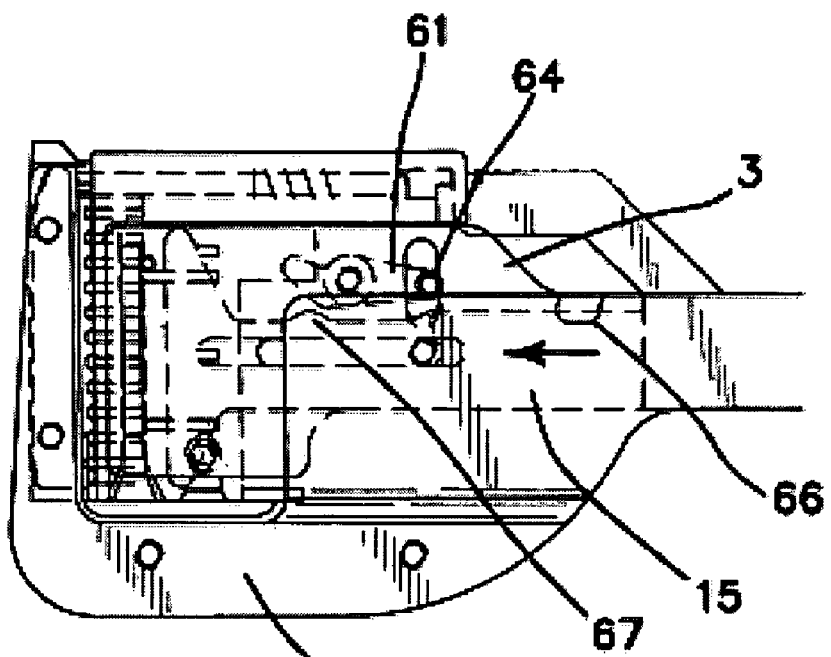

In FIGS. 40-41, the position of lever 61 is maintained as the capture or capture pin 31 is extended into the anvil. Likewise, as trigger 11 of actuator 9 and the jaws 4,5 are respectively moved to a capture position and subsequently to a closed position, the lever's position remains unchanged. Referring now to FIG. 42, as trigger 11 is manipulated to fire the stapler, the staple pusher 15 moves distally to push or drive the staples out of the cartridge 6. A projection or detent 67 extending from the staple pusher engages the lever 61 causing the lever 61 to pivot away from the staple pusher. Spring (not shown) assists in the pivoting of the lever, for example, by biasing the lever 61 in a clock-wise direction. The pin 64 slides along the aperture 65 until it contacts the frame preventing further rotation of the lever 61. As such, the lever 61 is generally parallel with the longitudinal axis of the staple and the frame 10.

Figure 43:
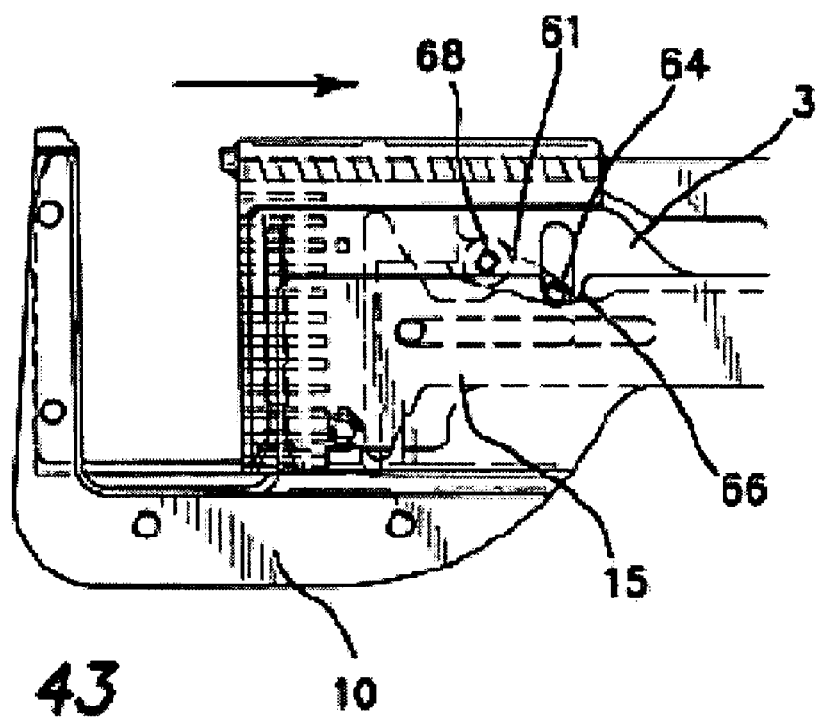
Figure 44:
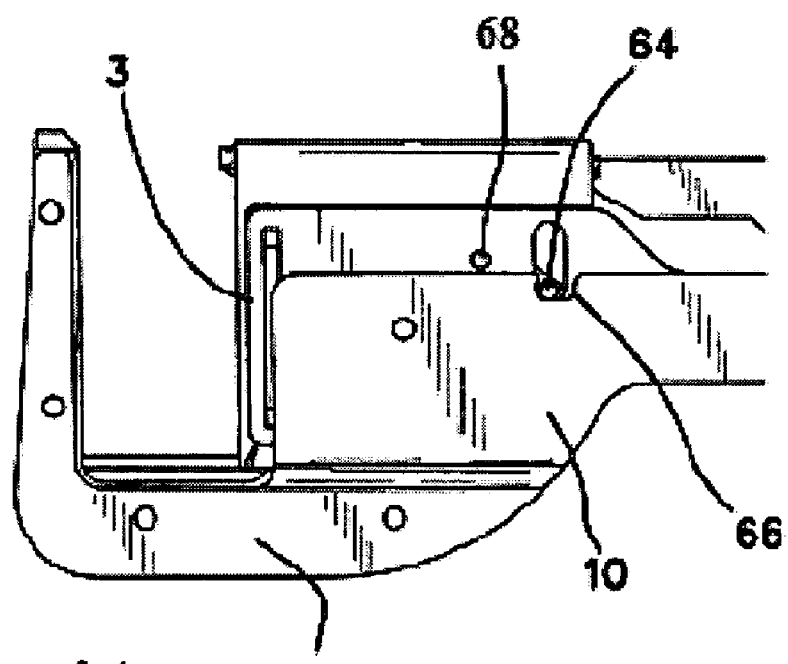

Referring now to FIGS. 43-44, after firing, the stapler is reset in which the capture pin 31 and jaws 4,5 retract. As the cartridge support 3 retracts, the pin 64 slides along the frame 10 until it reaches the slot 66 in which the lever 61 is then allowed to pivot back to its initial position. Pin 64 also slides along the aperture 65 until it reaches the end of the aperture 65. Pin 64 contacting the slot 66 in the frame prevents longitudinal movement of the cartridge support even if the trigger 11 is again actuated.

Accordingly, the present invention provides a surgical stapler. Although this invention has been described in certain specific embodiments, many additional modifications and variations would be apparent to those skilled in the art. It is therefore to be understood that this invention may be practiced otherwise than specifically described, including various changes in the size, shape and materials, without departing from the scope and spirit of the present invention. Thus, embodiments of the present invention should be considered in all respects as illustrative and not restrictive, the scope of the present invention to be determined by the appended claims and their equivalents rather than the foregoing description.

The invention claimed is:

1. A surgical stapler comprising:
   a shaft extending along a longitudinal axis having a proximal end and a distal end, a first jaw and a second jaw extending from the distal end of the shaft, the second jaw arranged to receive a staple cartridge having a plurality of staples and movable along the longitudinal axis towards the first jaw;
   an actuator coupled to the proximal end of the shaft; and
   a staple pusher coupled to the actuator and movable along the longitudinal axis to push the plurality of staples out of the cartridge along the longitudinal axis, the staple pusher having a distal portion and a proximal portion, the distal portion being pivotably connected to the proximal portion, the distal portion of the staple pusher having a first position and a second position, wherein when the distal portion of the staple pusher is in the first position movement of the staple pusher towards the first jaw is prevented;
   wherein the shaft comprises a cartridge support having a proximal end and a distal end being the second jaw, the proximal end having a first, second and third slots and a latch movable perpendicular to the longitudinal axis to be positioned sequentially in each of the first, second and third slots.

2. The stapler of claim 1 further comprising a rotatable cartridge lever connected to a frame, the cartridge support slidable within the frame.

3. The stapler of claim 1 further comprising a spring and a pivotable firing lever having a slot on one of the firing lever and the spring connected to another end of the firing lever biasing the firing lever in a horizontal position.

4. The stapler of claim 1 further comprising an actuator connected to the proximal end of the shaft, the actuator having a movable trigger and a stationary handle.

5. The stapler of claim 4 further comprising a rotatable firing lever lock having a slot, the rotatable firing lever lock operationally connected to the cartridge support and the slot operationally connected to a protrusion extending from the trigger.

6. The stapler of claim 4 further comprising a capture pin pusher being actuated by the movable trigger.

7. The stapler of claim 4 further comprising a release button connected to the stationary handle and operatively coupled to the latch and the release button movable in a first direction such that the latch moves perpendicular to the longitudinal axis to be disengaged from any of the first, second and third slots.

8. A surgical stapler comprising:
   a shaft extending along a longitudinal axis having a proximal end and a distal end, a first jaw and a second jaw extending from the distal end of the shaft, the second jaw arranged to receive a staple cartridge having a plurality of staples and the second jaw being movable towards the first jaw along the longitudinal axis;
   an actuator coupled to the proximal end of the shaft;
   a staple pusher coupled to the actuator and movable along the longitudinal axis to push the plurality of staples out of the cartridge along the longitudinal axis; and
   means for preventing longitudinal movement of the staple pusher, whereby longitudinal movement of the staple pusher is prevented when one of no cartridge is present in the second jaw and no staples are present in the cartridge occurs, wherein the means for preventing longitudinal movement of the staple pusher comprise a distal portion of the staple pusher pivotally connected to a proximal portion of the staple pusher.

9. A surgical stapler comprising:
   a shaft extending along a longitudinal axis having a proximal end and a distal end, a first jaw and a second jaw extending from the distal end of the shaft, the second jaw arranged to receive a staple cartridge having a plurality of staples and the second jaw being movable towards the first jaw along the longitudinal axis;
   an actuator coupled to the proximal end of the shaft;
   a staple pusher coupled to the actuator and movable along the longitudinal axis to push the plurality of staples out of the cartridge along the longitudinal axis; and
   means for preventing longitudinal movement of the staple pusher, whereby longitudinal movement of the staple pusher is prevented when one of no cartridge is present in the second jaw and no staples are present in the cartridge occurs, wherein the means for preventing longitudinal movement of the staple pusher comprise a pivotable latch connected to a pair of frame supports, the frame supports having a distal end connected to an anvil and a proximal end connected to the actuator.

10. The stapler of claim 9 wherein distal end of the frame support has an L-shaped slot and the pivotable latch has a projection movable within the L-shaped slot.

11. A surgical stapler comprising:
    a shaft extending along a longitudinal axis having a proximal end and a distal end, a first jaw and a second jaw extending from the distal end of the shaft, the second jaw arranged to receive a staple cartridge having a plurality of staples and the second jaw being movable towards the first jaw along the longitudinal axis;

an actuator coupled to the proximal end of the shaft;

a staple pusher coupled to the actuator and movable along the longitudinal axis to push the plurality of staples out of the cartridge along the longitudinal axis; and means for preventing longitudinal movement of the staple pusher, whereby longitudinal movement of the staple pusher is prevented when one of no cartridge is present in the second jaw and no staples are present in the cartridge occurs, wherein the means for preventing longitudinal movement of the staple pusher comprise a pivotable latch connected to the second jaw, the second jaw having a slot and the pivotable latch having a projection movable within the slot, the slot positioned perpendicular to the longitudinal axis of the second jaw.

12. The stapler of claim 11 wherein the shaft further comprises a frame support having a distal end forming the first jaw and the proximal end connected to the actuator, the frame having a slot, the projection of the pivotable latch movable into the slot of the frame in an initial position.

* * * * *